(12) United States Patent
Levner et al.

(10) Patent No.: US 11,067,571 B2
(45) Date of Patent: Jul. 20, 2021

(54) SURFACE FUNCTIONALIZATION

(71) Applicant: EMULATE, INC., Boston, MA (US)

(72) Inventors: Daniel Levner, Brookline, MA (US); S. Jordan Kerns, Reading, MA (US); Jefferson Puerta, Malden, MA (US)

(73) Assignee: EMULATE, INC., Boston, MA (US)

( * ) Notice: Subject to any disclaimer, the term of this patent is extended or adjusted under 35 U.S.C. 154(b) by 0 days.

(21) Appl. No.: 16/739,959

(22) Filed: Jan. 10, 2020

(65) Prior Publication Data
US 2020/0179928 A1    Jun. 11, 2020

Related U.S. Application Data

(63) Continuation of application No. PCT/US2018/041818, filed on Jul. 12, 2018.

(60) Provisional application No. 62/531,705, filed on Jul. 12, 2017.

(51) Int. Cl.
| | |
|---|---|
| *G01N 33/543* | (2006.01) |
| *C08J 7/04* | (2020.01) |
| *B05D 1/38* | (2006.01) |
| *B05D 3/06* | (2006.01) |
| *B05D 5/00* | (2006.01) |
| *C08J 7/12* | (2006.01) |
| *B01L 3/00* | (2006.01) |
| *C08J 7/043* | (2020.01) |

(52) U.S. Cl.
CPC .. *G01N 33/54393* (2013.01); *B01L 3/502707* (2013.01); *B05D 1/38* (2013.01); *B05D 3/067* (2013.01); *B05D 5/00* (2013.01); *C08J 7/043* (2020.01); *C08J 7/0427* (2020.01); *C08J 7/123* (2013.01); *B01L 2200/12* (2013.01); *B01L 2300/0883* (2013.01); *B01L 2300/165* (2013.01); *C08J 2323/32* (2013.01); *C08J 2353/02* (2013.01); *C08J 2423/32* (2013.01); *C08J 2471/02* (2013.01)

(58) Field of Classification Search
CPC .. B05D 1/38; B05D 3/067; B05D 5/00; B01L 3/502707; B01L 2200/12; B01L 2300/0883; B01L 2300/165; C08J 7/0427; C08J 7/123; C08J 2323/32; C08J 2353/02; C08J 2423/32; C08J 2471/02
See application file for complete search history.

(56) References Cited

U.S. PATENT DOCUMENTS

| | | | |
|---|---|---|---|
| 8,647,861 B2 | 2/2014 | Ingber et al. | 435/289.1 |
| 2007/0166771 A1 | 7/2007 | Kapur et al. | 435/287.2 |
| 2009/0068170 A1 | 3/2009 | Weitz et al. | 435/7.1 |
| 2009/0117166 A1* | 5/2009 | Myung | A61L 27/34 424/422 |

(Continued)

FOREIGN PATENT DOCUMENTS

| | | |
|---|---|---|
| WO | WO/2016/010861 | 1/2016 |
| WO | WO/2016/012778 | 1/2016 |
| WO | WO/2017/019799 | 2/2017 |

OTHER PUBLICATIONS

PCT International Search Report of International Application No. PCT/US2018/041818 dated Nov. 9, 2018.

*Primary Examiner* — Michael P Wieczorek
(74) *Attorney, Agent, or Firm* — Medlen & Carroll, LLP

(57) ABSTRACT

This invention is in the field of surface modification. In particular, the invention relates to the surface modification of microfluidic devices to alter surface hydrophobicity characteristics.

16 Claims, 13 Drawing Sheets

(56) References Cited

U.S. PATENT DOCUMENTS

| | | | |
|---|---|---|---|
| 2010/0009872 A1 | 1/2010 | Eid et al. | 506/16 |
| 2015/0209783 A1 | 7/2015 | Ingber et al. | 96/6 |
| 2018/0024120 A1* | 1/2018 | Levner | C12M 23/20 514/1.1 |

* cited by examiner

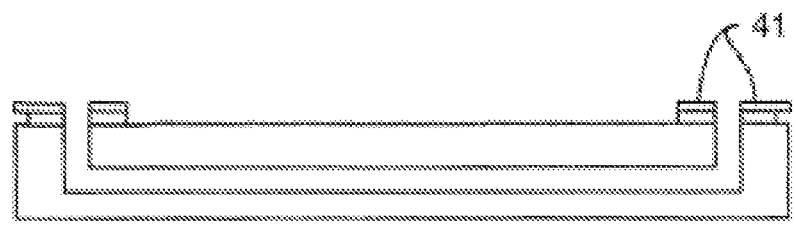
FIG.11A
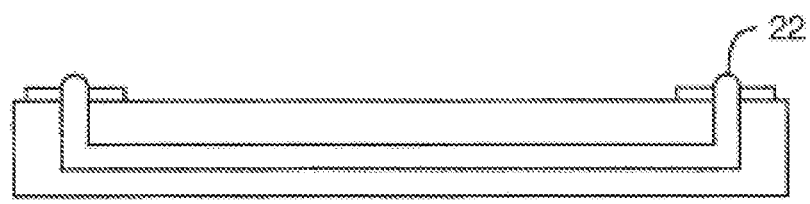
FIG.11B
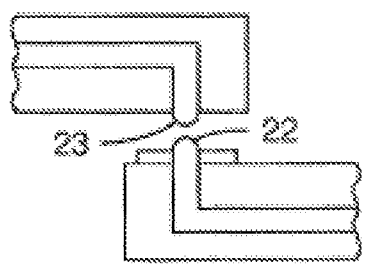 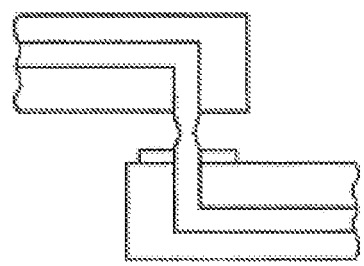
FIG.11C  FIG.11D

SURFACE FUNCTIONALIZATION

FIELD OF THE INVENTION

This invention is in the field of surface modification by functionalization. In particular, the invention relates to the surface modification of microfluidic devices to alter surface hydrophobicity characteristics.

BACKGROUND OF THE INVENTION

Microfluidic devices have been used for multiple applications, but are often limited by the characteristics of the device materials and physical properties of the surfaces with such devices. What is needed is a way to modify surfaces with such devices so that such surface physical properties may be specifically designed.

SUMMARY OF THE INVENTION

This invention is in the field of surface modification by functionalization. In particular, the invention relates to the surface modification of microfluidic devices to alter surface hydrophobicity characteristics. In one embodiment, the present invention contemplates a method of functionalizing the surface of a microfluidic substrate comprising a) providing i) a microfluidic substrate comprising a surface; ii) a bifunctional crosslinker; and iii) surface hydrophobicity modifying molecules; b) exposing at least a portion of said surface of said substrate to said bifunctional crosslinker; c) activating said crosslinker under first conditions to create a crosslinked substrate surface; and d) exposing said crosslinked substrate surface to said surface hydrophobicity modifying molecules under second conditions to create a functionalized substrate surface, (n one embodiment, said bifunctional crosslinker comprises a heterobifunctional crosslinker. In one embodiment, said substrate is a portion of a microfluidic device, in one embodiment, said portion of a microfluidic device is selected from the group consisting of a layer, a membrane, a channel, a reservoir, a port and a resistor, in one embodiment, the resistor has serpentine microchannels. In one embodiment, said first conditions comprise exposing said crosslinker to light. In one embodiment, said exposure to light comprises rastering or pattern projection. In one embodiment, said light is UV tight, in one embodiment, step c) is followed by a washing step before step d), e.g. to remove unreacted crosslinker. In one embodiment, step d) is followed by a washing step, e.g. to remove unreacted surface modifying molecules. In a preferred embodiment, said activating of step c) is done without heat. In a preferred embodiment, said activating of step c) is done without added heat, in one embodiment, said activating of step c) is done at a temperature of 37° C. or below, in one embodiment, said second conditions comprise exposure at temperatures at or below room temperature (without the need for added heat or UV light). In a preferred embodiment, said activating of step c) is done at room temperature. In one embodiment, said microfluidic substrate surface comprises a thermoplastic material. In one embodiment, said thermoplastic material is selected from the group consisting of cyclo olefin polymer, polydimethylsiloxane, and polycarbonate. In one embodiment, said surface hydrophobicity modifying molecules are selected from hydrophilic molecules or hydrophobic molecules. In one embodiment, hydrophilic molecules are selected from the group consisting of PEG, TRIS, poly vinyl alcohol, and PLA. In one embodiment, said hydrophobic molecules are selected from the group consisting of alkanes, fluorocarbons, fluorinated polymers (or fluoropolymers) and nylon. In one embodiment, said fluorinated polymers are selected from the group consisting of polytetrafluoroethylene (PTFE) and fluorinated ethylene propylene (FEP). In one embodiment, bifunctional crosslinkers are used. In one embodiment, said crosslinker is selected from the group consisting of: N-5-azido-2-nitrobenzoyloxysuccinimide (ANB-NOS), sulfosuccinimidyl 2-[m-azido-o-nitrobenzamido]ethyl-1, 3'-dithiopropionate (Sulfo-SAND), N-succinimidyl-6-[4'-azido-2'-nitrophenylamino] hexanoate (SANPAH) and sulfosuccinimidyl-6-[4'-azido-2'-nitrophenylamino]hexanoate (Sulfo-SANPAH).

It is not intended that the present invention be limited to functionalizing an entire component of a microfluidic device or an entire surface of a component. In one embodiment, the invention relates to the modification of a region or portion of a component (e.g. a region on the surface, including but not limited to a region surrounding an inlet or outlet port) of a microfluidic devices to alter surface hydrophobicity characteristics, in one embodiment, the present invention contemplates a method of functionalizing (a region or portion of) the surface of a microfluidic substrate comprising; a) providing i) a microfluidic substrate comprising a surface; ii) a bifunctional crosslinker; and iii) surface hydrophobicity modifying molecules; b) masking a region (or portion) of said surface of said substrate so as to create a masked portion and an unmasked portion; c) exposing said unmasked portion of said surface of said substrate to said bifunctional crosslinker; d) activating said crosslinker under first conditions to create a crosslinked substrate surface in said unmasked portion; and e) exposing said crosslinked substrate surface to said surface hydrophobicity modifying molecules under second conditions to create a functionalized substrate surface in said unmasked portion. In one embodiment, said substrate is a component of a microfluidic device. In one embodiment, said component of a microfluidic device is selected from the group consisting of a layer, a membrane, a channel, a reservoir, a port and a resistor. In one embodiment, the resistor has serpentine microchannels. In one embodiment, said first conditions comprise exposing said crosslinker to light. In one embodiment, the portion not exposed to the crosslinker was covered with a mask and the portion exposed to the crosslinker was unmasked. The mask may be adhesive material (e.g. tape) or non-adhesive material (e.g. metal or metal foil such as aluminum foil). In one embodiment, said second conditions comprise exposure at temperatures at or below room temperature (without the need to added heat or UV light). In one embodiment, said exposure to light comprises rastering or pattern projection. In one embodiment, said light is UV light, in one embodiment, step d) is followed by a washing step before step e), e.g. to remove unreacted crosslinker. In one embodiment, step e) is followed by a washing step, e.g. to remove unreacted surface modifying molecules. In a preferred embodiment, said activating of step d) is done without heat. In a preferred embodiment, said activating of step d) is done without added heat. In one embodiment, said activating of step d) is done at a temperature of 37° C. or below. In a preferred embodiment, said activating of step d) is done at room temperature or below (without any added heat). In one embodiment, said microfluidic substrate surface comprises a thermoplastic material. In one embodiment, said thermoplastic material is selected from the group consisting of cyclo olefin polymer, polydimethylsiloxane, and polycarbonate. In one embodiment, said surface hydrophobicity modifying molecules are selected from hydrophilic molecules or hydrophobic molecules. In one embodiment, said hydrophilic molecules are selected from the group consisting of PEG, TRIS, poly vinyl alcohol, and PLA. In one embodiment, said hydrophobic molecules are selected from the group consisting of alkanes, fluorocarbons, fluorinated polymers (or fluoropolymers) and nylon. In one embodiment, said fluorinated polymers are selected from the group consisting of Polytetrafluoroethylene (PTFE) and fluorinated ethylene propylene (FEP). In one embodiment, said crosslinker is selected from the group consisting of: ANB-NOS, Sulfo-SAND, SANPAH and Sulfo-SANPAH.

As noted above, it is not intended that the present invention be limited to functionalizing an entire component of a microfluidic device or an entire surface of a component. In one embodiment, the invention relates to the modification of a region or portion of a component (e.g. a region on the surface, including but not limited to a region surrounding an inlet or outlet port) of a microfluidic devices to alter surface hydrophobicity characteristics. In one embodiment, a mask is used for this purpose. However, it is not intended that the present invention be limited to how a mask is used. In one embodiment, the present invention contemplates a method of functionalizing the surface of a microfluidic substrate comprising: a) providing i) a microfluidic substrate comprising a surface; ii) a bifunctional crosslinker, and iii) surface hydrophobicity modifying molecules; b) exposing said surface of said substrate to said bifunctional crosslinker; c) masking a portion of said surface of said substrate so as to create a masked portion and an unmasked portion; d) activating said crosslinker with light in said unmasked portion to create a crosslinked substrate surface portion; and e) exposing said crosslinked substrate surface portion to said surface hydrophobicity modifying molecules under second conditions to create a functionalized substrate surface portion. In one embodiment, said substrate is a component of a microfluidic device. In one embodiment, said component of a microfluidic device is selected from the group consisting of a layer, a membrane, a channel, a reservoir, a port and a resistor. In one embodiment, the resistor has serpentine microchannels. In one embodiment, said first conditions comprise exposing said crosslinker to light. In one embodiment, the portion where the crosslinker is not attached was covered with a mask (e.g. the crosslinker is light activated and the mask blocks the light, such that the crosslinker does not react with the surface and attach) and the portion where the crosslinker is attached was unmasked. The mask may be adhesive material (e.g. tape) or non-adhesive material (e.g. metal or metal foil such as aluminum foil). In one embodiment, said second conditions comprise exposure at temperatures at or below room temperature (without added heat or UV light). In one embodiment, said exposure to fight comprises rastering or pattern projection. In one embodiment, said light is UV light, in one embodiment, step d) is followed by a washing step before step e), e.g. to remove unreacted crosslinker. In one embodiment, step e) is followed by a washing step, e.g. to remove unreacted surface modifying molecules. In a preferred embodiment, said activating of step d) is done without heat. In a preferred embodiment, said activating of step d) is done without added heat. In one embodiment, said activating of step d) is done at a temperature of 37° C. or below. In a preferred embodiment, said activating of step d) is done at room temperature or below (without any added heat). In one embodiment, said microfluidic substrate surface comprises a thermoplastic material. In one embodiment, said thermoplastic material is selected from the group consisting of cyclo olefin polymer, polydimethylsiloxane, and polycarbonate. In one embodiment, said surface hydrophobicity modifying molecules are selected from hydrophilic molecules or hydrophobic molecules. In one embodiment, said hydrophilic molecules are selected from the group consisting of PEG, TRIS, poly vinyl alcohol, and PLA. In one embodiment, said hydrophobic molecules are selected from the group consisting of alkanes, fluorocarbons, fluorinated polymers (or fluoropolymers) and nylon. In one embodiment, said fluorinated polymers are selected from the group consisting of polytetrafluoroethylene (PTFE) and fluorinated ethylene propylene (FEP). In one embodiment, said crosslinker is selected from the group consisting of: ANB-NOS, Sulfo-SAND, SANPAH and Sulfo-SANPAH.

As noted above, it is not intended that the present invention be limited to functionalizing an entire component of a microfluidic device or an entire surface of a component. In one embodiment, the invention relates to a method comprising: a) providing i) a first fluidic device comprising a substrate having a first mating surface, said first mating surface comprising one or more fluidic ports, ii) a fluid source comprising fluid, and iii) a second fluidic device comprising a second mating surface; iv) a bifunctional crosslinker; v) surface hydrophobicity modifying molecules; b) exposing a portion of the first mating surface surrounding a fluidic port to said bifunctional crosslinker; c) activating said crosslinker under first conditions to create a crosslinked first mating surface; and d) exposing said crosslinked first mating surface to said surface hydrophobicity modifying molecules under second conditions to create a functionalized first mating surface, wherein said treated first mating surface is adapted to stably retain one or more liquid droplets; and e) introducing fluid into said first fluidic device such that a liquid droplet is stably retained at one fluidic ports. In one embodiment, the method further comprises a step f) positioning said treated first mating surface of said first fluidic device to engage said second mating surface on a second fluidic device. In one embodiment, said second mating surface comprising one or more fluidic ports. In one embodiment, said second mating surface is functionalized as in steps b) to d). In one embodiment, at least portion of said first mating surface is masked from surface functionalization. In one embodiment, a region adjacent to said first mating surface is masked from surface functionalization. For Example, see FIG. 11A-D regarding masking mating surfaces. In one embodiment, said first mating surface comprises a droplet. In one embodiment, said functionalized substrate surface creates stable droplets, or droplets that do not change position or volume due to external forces, like gravity or the rocking/shaking of said surfaces.

As noted above, it is not intended that the present invention be limited to functionalizing an entire component of a microfluidic device or an entire surface of a component. In one embodiment, the invention relates to a method of controlling cell seeding in a microfluidic device, comprising: a) providing i) a microfluidic device with one or more speeding channels in fluidic communication with a cell growth area, said seeding channels comprising walls; ii) a bifunctional crosslinker; iii) surface hydrophobicity modifying molecules: iv) cells; and v) a mask; b) masking the cell growth area of said microfluidic device with said mask so as to create a masked cell growth area and an unmasked portion of said microfluidic device comprising said seeding channels; c) exposing said unmasked portion of said microfluidic device to said bifunctional crosslinker; d) activating said crosslinker under first conditions to create a crosslinked microfluidic device surface in said unmasked portion; e) exposing said crosslinked microfluidic device surface to said surface hydrophobicity modifying molecules under second conditions to create a functionalized microfluidic device surface in said unmasked portion; and f) adding cells to said seeding channel, wherein a majority of the cells do not attach to the seeding channel, but attach to the growth area. In one embodiment, step d) is followed by a washing step before step e), e.g. to remove unreacted crosslinker. In one embodiment, step e) is followed by a washing step, e.g. to remove unreacted surface modifying molecules. In a preferred embodiment, said activating of step d) is done without heat. In a preferred embodiment, said activating of step d) is done without added heat. In one embodiment, said activating of step d) is done at a temperature of 37° C. or below. In one embodiment, said second conditions of step e) comprise exposure at temperatures at or below room temperature (without the need for added heat or UV light). In a preferred embodiment, said activating of step d) is done at room temperature or below. In one embodiment, said cell growth area comprises a membrane. In one embodiment, said cell growth area comprises a central channel. In one embodiment, said hydrophobicity modifying molecules comprise polyethyleneglycol. In one embodiment, said hydrophobicity modifying molecules comprise TRIS. In one embodiment, said crosslinker is introduced in solution to said unmasked portion in step c). In one embodiment, said first conditions of step d) comprise exposing said unmasked portion to UV light. In one embodiment, said exposing to UV light is done through said walls of said seeding channel (e.g. without opening the device).

As noted above, it is not intended that the present invention be limited to functionalizing an entire component of a microfluidic device or an entire surface of a component. In one embodiment, the invention relates to a method of controlling cell seeding in a microfluidic device comprising: a) providing i) a microfluidic device with one or more seeding channels in fluidic communication with a cell growth area, said seeding channels comprising walls; ii) a bifunctional crosslinker; iii) surface hydrophobicity modifying molecules; iv) cells; and v) a mask; b) exposing said seeding channels and said growth area to said bifunctional crosslinker; c) masking the cell growth area of said microfluidic device with said mask so as to create a masked cell growth are, wherein said seeding channels are unmasked; d) exposing said microfluidic device to UV light so as to activate said bifunctional crosslinker in said unmasked seeding channels so as to create crosslinked surfaces, wherein said mask blocks the UV light from contacting said cell growth area; e) exposing said crosslinked surfaces of said seeding channels to said surface hydrophobicity modifying molecules under conditions such that functionalized seeding channel surfaces are created; and f) adding cells to said seeding channel, wherein a majority of the cells do not attach to the seeding channel, but attach to the growth area. In one embodiment, step d) is followed by a washing step before step e), e.g. to remove unreacted crosslinker. In one embodiment, step e) is followed by a washing step, e.g. to remove unreacted surface modifying molecules. In a preferred embodiment, said exposing to UV light of step d) is done without heat. In a preferred embodiment, it is done without added heat. In one embodiment, it is done at a temperature of 37° C. or below. In one embodiment, said second conditions comprise exposure at temperatures at or below room temperature (without the need for added heat or UV light). In a preferred embodiment, said exposing to UV light is done at room temperature. In one embodiment, said cell growth area comprises a membrane. In one embodiment, said cell growth area comprises a central channel. In one embodiment, said hydrophobicity modifying molecules comprise polyethyleneglycol. In one embodiment, said hydrophobicity modifying molecules comprise TRIS. In one embodiment, said crosslinker is introduced in solution into said microfluidic device in step b). In one embodiment, said bifunctional crosslinker is Sulfo-SANPAH. In one embodiment, said exposing to UV light of step d) is done through said walls of said seeding channels (e.g. without opening the device).

As noted above, it is not intended that the present invention be limited to functionalizing an entire component of a microfluidic device or an entire surface of a component. In one embodiment, the invention relates to a method of functionalizing the surface of a microfluidic substrate comprising the steps of: a) providing; i) a microfluidic substrate comprising an unmodified surface comprising naturally occurring moieties; ii) a bifunctional crosslinker; iii) surface hydrophobicity modifying molecules; b) exposing at least a portion of said surface of said substrate to said bifunctional crosslinker; c) activating said crosslinker under first conditions to create a crosslinked substrate surface, wherein said crosslinker reacts with said naturally occurring moieties on said unmodified surface; and d) exposing said crosslinked substrate surface to said surface hydrophobicity modifying molecules under second conditions to create a functionalized substrate surface. In one embodiment, the moieties on the unmodified surface are not the result of pretreatment. In one embodiment, said substrate is a portion of a microfluidic device. In one embodiment, said portion of a microfluidic device is selected from the group consisting of a layer, a membrane, a channel, a reservoir, a port and a resistor. In one embodiment, said resistor comprises a serpentine channel. In one embodiment, said serpentine channel, after step d), is more hydrophilic than said unmodified surface. In one embodiment, said serpentine channel comprises a bubble. In one embodiment, said functionalized substrate surface improves the clearance of said bubble compared to the unmodified surface. In one embodiment, said functionalized substrate surface improves the clearance of said bubble when pressure is applied to said bubble. In one embodiment, said functionalized substrate surface improves the clearance of said bubble when said bubble is exposed to fluid at a flow rate. In one embodiment, said crosslinker is photoactivatable. In one embodiment, said first conditions comprise exposing said crosslinker to light. In one embodiment, said exposure to light comprises rastering or pattern projection. In one embodiment, said light is UV light. In one embodiment, step c) is followed by a washing step before step d). In one embodiment, step d) is followed by a washing step. In one embodiment, said activating of step c) is done at room temperature or below, in one embodiment, said activating of step c) is done at room temperature. In one embodiment, said activating of step c) is done without added heat. In one embodiment, said microfluidic substrate surface comprises a thermoplastic material. In one embodiment, said thermoplastic material is selected from the group consisting of cyclo olefin polymer, polydimethylsiloxane, and polycarbonate. In one embodiment, said surface hydrophobicity modifying molecules are selected from the group consisting of hydrophilic molecules and hydrophobic molecules. In one embodiment, said hydrophilic molecules are selected from the group consisting of PEG, TRIS, poly vinyl alcohol, and PLA. In one embodiment, said hydrophobic molecules are selected from the group consisting of alkanes, fluorocarbons, fluorinated polymers and nylon. In one embodiment, said fluorinated polymers are selected from the group consisting of PTFE and FEP. In one embodiment, said crosslinker is selected from the group consisting of: ANB-NOS, Sulfo- SAND, SANPAH and Sulfo-SANPAH. In one embodiment, said PEG is an amine-terminated PEG. In one embodiment, said functionalized substrate surface comprising PEG is more hydrophilic than the unmodified surface. In one embodiment, said method further comprises step e) wherein said microfluidic substrate is seeded with cells. In one embodiment, said functionalized substrate surface prevents cell attachment. In one embodiment, said functionalized substrate surface promotes cell attachment. In one embodiment, said naturally occurring moieties are selected from the group consisting of double bonds, C—H sites, N—H sites, and nucleophiles. In one embodiment, said nucleophiles are selected from the group consisting of primary amines, alcohols, azide, amines, and amides.

As noted above, it is not intended that the present invention be limited to functionalizing an entire component of a microfluidic device or an entire surface of a component. In one embodiment, the invention relates to a method of functionalizing the surface of a microfluidic substrate comprising the steps of; a) providing; i) a microfluidic substrate comprising an unmodified surface comprising naturally occurring moieties; ii) a bifunctional crosslinker; iii) surface hydrophobicity modifying molecules; b) masking a region of said surface of said substrate so as to create a masked portion and an unmasked portion; c) exposing said unmasked portion of said surface of said substrate to said bifunctional crosslinker, wherein said crosslinker reacts with said naturally occurring moieties on said unmodified surface; d) activating said crosslinker under first conditions to create a crosslinked substrate surface in said unmasked portion; and e) exposing said crosslinked substrate surface to said surface hydrophobicity modifying molecules under second conditions to create a functionalized substrate surface in said unmasked portion. In one embodiment, the moieties on the unmodified surface are not the result of pretreatment. It is not intended that the present invention be limited to the nature or number of naturally occurring moieties. In one embodiment, naturally occurring moieties are selected from the group consisting of double bonds, C—H sites, N—H sites, and nucleophiles. In one embodiment, said nucleophiles are selected from the group consisting of primary amines, alcohols, azide, amines, and amides. In one embodiment, said substrate is a component of a microfluidic device. In one embodiment, said component of a microfluidic device is selected from the group consisting of a layer, a membrane, a channel, a reservoir, a port and a resistor. In one embodiment, said crosslinker is photoactivatable. In one embodiment, said first conditions comprise exposing said crosslinker to light. In one embodiment, said light is UV light. In one embodiment, said exposure to light comprises pattern projection. In one embodiment, said exposure to light comprises rastering. In one embodiment, activating of step d) is done without added heat. In one embodiment, said masking is performed with an adhesive substance. In one embodiment, said method further comprises the step f) removing the adhesive substance. In one embodiment, step d) is followed by a washing step before step e). In one embodiment, step e) is followed by a washing step. In one embodiment, said microfluidic substrate surface comprises a thermoplastic material. In one embodiment, said thermoplastic material is selected from the group consisting of cyclo olefin polymer, polydimethylsiloxane, and polycarbonate. In one embodiment, said surface hydrophobicity modifying molecules are selected from the group consisting of hydrophilic molecules and hydrophobic molecules. In one embodiment, said hydrophilic molecules are selected from the group consisting of PEG, TRIS, poly vinyl alcohol, and PLA. In one embodiment, said hydrophobic molecules are selected from the group consisting of alkanes of various lengths, fluorocarbons, various fluorinated materials (PTFE, FEP, etc.), and selected nylons. In one embodiment, said crosslinker is selected from the group consisting of: ANB-NOS, Sulfo-SAND, SANPAH and Sulfo-SANPAH. In one embodiment, said bifunctional crosslinker is Sulfo-SANPAH and said surface hydrophobicity modifying molecule is an amine-terminated PEG. In one embodiment, said crosslinker comprises light-reactive portion, a linker, and a modifier-reactive portion. In one embodiment, said light reactive portion is selected from the group consisting of nitrophenyl, diazirine, and azides. In one embodiment, said linker is selected from the group consisting of alkyl group, disulfide, and olefins. In one embodiment, said modifier-reactive portion is selected from the group consisting of NHS-ester (amine reactive), sulfo-NHS-ester (amine reactive), isocyanate (amine reactive), isothiocyanate (amine reactive), imidoester (amine reactive), maleimide (sulfhydryl reactive), pyridyldithiol (sulfhydryl reactive), and hydrazide (aldehyde and ketone reactive).

As noted above, it is not intended that the present invention be limited to functionalizing an entire component of a microfluidic device or an entire surface of a component. In one embodiment, the invention relates to a method of functionalizing the surface of a microfluidic substrate comprising the steps; a) providing: i) a microfluidic substrate comprising an unmodified surface comprising naturally occurring moieties; ii) a photoactivatable bifunctional crosslinker; iii) surface hydrophobicity modifying molecules; b) exposing said surface of said substrate to said bifunctional crosslinker; c) masking a region of said surface of said substrate so as to create a masked portion and an unmasked portion; d) activating said crosslinker with light in said unmasked portion to create a crosslinked substrate surface portion; and e) exposing said crosslinked substrate surface portion to said surface hydrophobicity modifying molecules under second conditions to create a functionalized substrate surface portion, wherein said crosslinker reacts with said naturally occurring moieties on said unmodified surface. In one embodiment, the moieties on the unmodified surface are not the result of pretreatment. In one embodiment, said naturally occurring moieties are selected from the group consisting of double bonds, C—H sites. N—H sites, and nucleophiles. In one embodiment, said nucleophiles are selected from the group consisting of primary amines, alcohols, azide, amines, and amides. In one embodiment, said substrate is selected from the group consisting of a channel, a reservoir and a resistor. In one embodiment, activating of step d) is done without added heat In one embodiment, said masking is performed with an adhesive substance. In one embodiment, said method further comprises the step f) removing the adhesive substance. In one embodiment, said light is UV light. In one embodiment, said exposure to light comprises pattern projection. In one embodiment, said exposure to light comprises rastering. In one embodiment, step d) is followed by a washing step before step e). In one embodiment, step e) is followed by a washing step. In one embodiment, said microfluidic substrate surface comprises a thermoplastic material. In one embodiment, said thermoplastic material is selected from the group consisting of cyclo olefin polymer, polydimethylsiloxane, and polycarbonate. In one embodiment, said surface hydrophobicity modifying molecules are selected from the group consisting of hydrophilic molecules and hydrophobic molecules. In one embodiment, said hydrophilic molecules are selected from the group consisting of PEG, TRIS, poly vinyl alcohol, and PLA. In one embodiment, said hydrophobic molecules are selected from the group consisting of alkanes of various lengths, fluorocarbons, various fluorinated materials (PTFE, PEP, etc.), and selected nylons. In one embodiment, said crosslinker is selected from the group consisting of: ANB-NOS, Sulfo-SAND, SANPAH and Sulfo-SANPAH. In one embodiment, said crosslinker is Sulfo-SANPAH and said surface hydrophobicity modifying molecule is an amine-terminated PEG. In one embodiment, said crosslinker comprises light-reactive portion, a linker, and a modifier-reactive portion. In one embodiment, said light reactive portion is selected from the group consisting of nitrophenyl, diazirine, and azides. In one embodiment, said linker is selected from the group consisting of alkyl group, disulfide, and olefins. In one embodiment, said modifier-reactive portion is selected from the group consisting of NHS-ester (amine reactive), sulfo-NHS-ester (amine reactive), isocyanate (amine reactive), isothiocyanate (amine reactive), imidoester (amine reactive), maleimide (sulfhydryl reactive), pyridyldithiol (sulfhydryl reactive), and hydrazide (aldehyde and ketone reactive).

As noted above, it is not intended that the present invention be limited to functionalizing an entire component of a microfluidic device or an entire surface of a component. In one embodiment, the invention relates to a method comprising: a) providing i) a first fluidic device comprising a substrate having a first mating surface, said first mating surface comprising one or more fluidic ports, ii) a fluid source comprising fluid, and iii) a second fluidic device comprising a second mating surface; iv) a bifunctional crosslinker; v) surface hydrophobicity modifying molecules; b) exposing a portion of the first mating surface surrounding a fluidic port to said bifunctional crosslinker; c) activating said crosslinker under first conditions to create a crosslinked first mating surface; and d) exposing said crosslinked first mating surface to said surface hydrophobicity modifying molecules under second conditions to create a functionalized first mating surface, wherein said treated first mating surface is adapted to stably retain one or more liquid droplets; and e) introducing fluid into said first fluidic device such that a liquid droplet is stably retained at one fluidic port. In one embodiment, said method further comprises the step f) positioning said treated first mating surface of said first fluidic device to engage said second mating surface on a second fluidic device. In one embodiment, said second mating surface comprising one or more fluidic ports. In one embodiment, said second mating surface is functionalized as in steps b) to d). In one embodiment, at least portion of said first mating surface is masked from surface functionalization. In one embodiment, a region adjacent to said first mating surface is masked from surface functionalization. In one embodiment, said second mating surface comprises a droplet.

As noted above, it is not intended that the present invention be limited to functionalizing an entire component of a microfluidic device or an entire surface of a component. In one embodiment, the invention relates to a method of controlling cell seeding in a microfluidic device, comprising: a) providing i) a microfluidic device with one or more sealing channels in fluidic communication with a cell growth area, said seeding channels comprising walls and one or more unmodified surfaces comprising naturally occurring moieties; ii) a bifunctional crosslinker; iii) surface hydrophobicity modifying molecules; iv) cells; and v) a mask; b) masking the cell growth area of said microfluidic device with said mask so as to create a masked cell growth area and an unmasked portion of said microfluidic device comprising said seeding channels; c) exposing said unmasked portion of said microfluidic device to said bifunctional crosslinker, wherein said crosslinker reacts with naturally occurring moieties on said one or more unmodified surfaces; d) activating said crosslinker under first conditions to create a crosslinked microfluidic device surface in said unmasked portion; e) exposing said crosslinked microfluidic device surface to said surface hydrophobicity modifying molecules under second conditions to create a functionalized microfluidic device surface in said unmasked portion; and f) adding cells to said seeding channel, wherein a majority of the cells do not attach to the seeding channels, but attach to the cell growth area. In one embodiment, the moieties on the unmodified surface are not the result of pretreatment. In one embodiment, said naturally occurring moieties are selected from the group consisting of double bonds, C—H sites, N—H sites, and nucleophiles. In one embodiment, said nucleophiles are selected from the group consisting of primary amines, alcohols, azide, amines, and amides. In one embodiment, said crosslinker is photoactivatable. In one embodiment, said cell growth area comprises a membrane. In one embodiment, said cell growth area comprises a central channel. In one embodiment, said hydrophobicity modifying molecules comprise polyethyleneglycol. In one embodiment, said hydrophobicity modifying molecules comprise TRIS. In one embodiment, said crosslinker is introduced in solution to said unmasked portion in step c). In one embodiment, said first conditions of step d) comprises exposing said unmasked portion to UV light, in one embodiment, said exposing to UV light is done through said walls of said seeding channel.

As noted above, it is not intended that the present invention be limited to functionalizing an entire component of a microfluidic device or an entire surface of a component. In one embodiment, the invention relates to a method of controlling cell seeding in a microfluidic device comprising: a) providing i) a microfluidic device with one or more seeding channels in fluidic communication with a cell growth area, said seeding channels comprising walls and surfaces; ii) a photoactivatable bifunctional crosslinker; iii) surface hydrophobicity modifying molecules; iv) cells; and v) a mask; b) exposing said seeding channels and said growth area to said photoactivatable bifunctional crosslinker; c) masking the cell growth area of said microfluidic device with said mask so as to create a masked cell growth area, wherein said seeding channels are unmasked; d) exposing said microfluidic device to UV light so as to activate said photoactivatable bifunctional crosslinker in said unmasked seeding channels so as to create crosslinked surfaces, wherein said mask blocks the UV light from contacting said cell growth area; e) exposing said crosslinked surfaces of said seeding channels to said surface hydrophobicity modifying molecules under conditions such that functionalized seeding channel surfaces are created; and f) adding cells to said seeding channel, wherein a majority of the cells do not attach to the seeding channels, but attach to the growth area. In one embodiment, said cell growth area comprises a membrane. In one embodiment, said cell growth area comprises a central channel. In one embodiment, said hydrophobicity modifying molecules comprise polyethyleneglycol. In one embodiment, said hydrophobicity modifying molecules comprise TRIS. In one embodiment, said crosslinker is introduced in solution into said microfluidic device in step b). In one embodiment, said photoactivatable bifunctional crosslinker is Sulfo-SANPAH. in one embodiment, said exposing to UV light of step d) is done through said walls of said seeding channels.

As noted above, it is not intended that the present invention be limited to functionalizing an entire component of a microfluidic device or an entire surface of a component. In one embodiment, the invention relates to a method detecting and clearing a bubble on a microfluidic substrate comprising: a) providing; i) a microfluidic substrate comprising an unmodified surface comprising naturally occurring moieties; ii) a bifunctional crosslinker; iii) surface hydrophobicity modifying molecules; b) exposing at least a portion of said surface of said substrate to said bifunctional crosslinker; c) activating said crosslinker under first conditions to create a crosslinked substrate surface, wherein said crosslinker reacts with naturally occurring moieties on said unmodified surface; d) exposing said crosslinked substrate surface to said surface hydrophobicity modifying molecules under second conditions to create a functionalized substrate surface; e) detecting a bubble upon said functionalized substrate surface; and f) clearing said bubble such that it docs not contact said functionalized substrate surface.

In one embodiment, the moieties on the unmodified surface are not the result of presentment. In one embodiment, said naturally occurring moieties are selected from the group consisting of double bonds, C—H sites, N—H sites, and nucleophiles. In one embodiment, said nucleophiles are selected from the group consisting of primary amines, alcohols, azide, amines, and amides. In one embodiment, said substrate is a component of a microfluidic device. In one embodiment, said component of a microfluidic device is selected from the group consisting of a layer, a membrane, a channel, a reservoir, a port and a resistor. In one embodiment, said resistor comprises a serpentine channel. In one embodiment, said serpentine channel surface after step d) is more hydrophilic than said unmodified surface. In one embodiment, said bubble is detected in said serpentine channel. In one embodiment, said bubbles do not stick (or resist movement) to said functionalized substrate surface. In one embodiment, said functionalized substrate surface improves the clearance of said bubble compared to the unfunctionalized surface. In one embodiment, said functionalized substrate surface improves the clearance of said bubble when pressure is applied to said bubble. In one embodiment, said functionalized substrate surface improves the clearance of said bubble when raid bubble is exposed to fluid at a flow rate. In one embodiment, said crosslinker is photoactivatable. In one embodiment, said first conditions comprise exposing said crosslinker to light. In one embodiment, said exposure to light comprises rastering or pattern projection. In one embodiment, said light is UV light. In one embodiment, step c) is followed by a washing step before step d). In one embodiment, step d) is followed by a washing step. In one embodiment, said activating of step c) is done at room temperature or below. In one embodiment, said activating of step c) is done at room temperature. In one embodiment, said activating of step c) is done without added heat. In one embodiment, said microfluidic substrate surface comprises a thermoplastic material. In one embodiment, said thermoplastic material is selected from the group consisting of cyclo olefin polymer, polydimethylsiloxane, and polycarbonate. In one embodiment, said surface hydrophobicity modifying molecules are selected from the group consisting of hydrophilic molecules and hydrophobic molecules. In one embodiment, said hydrophilic molecules are selected from the group consisting of PEG, TRIS, poly vinyl alcohol, and PLA. In one embodiment, said hydrophobic molecules are selected from the group consisting of alkanes, fluorocarbons, fluorinated polymers and nylon. In one embodiment, said fluorinated polymers are selected from the group consisting of PTFE and FEP. In one embodiment, said crosslinker is selected from the group consisting of: ANB-NOS, Sulfo-SAND, SANPAH and Sulfo-SANPAH. In one embodiment, said hydrophilic molecule is an amine-terminated PEG. In one embodiment, said functionalized substrate surface is more hydrophilic than the unfunctionalized surface. In one embodiment, said method further comprises, either after step d) or step f), wherein said microfluidic substrate is seeded with cells. In one embodiment, said functionalized substrate surface prevents cell attachment. In one embodiment, said functionalized substrate surface promotes cell attachment.

DEFINITIONS

To facilitate the understanding of this invention, a number of terms are defined below. A surface or a region on a surface is "hydrophobic" when it displays (e.g. advancing) contact angles for water greater than approximately ninety (90) degrees (in many cases, it is preferable that both advancing and receding contact angles are greater than approximately 90 degrees). In one embodiment, the hydrophobic surfaces of the present invention display advancing contact angles for water between approximately ninety (90) and approximately one hundred and ten (110) degrees, in another embodiment, hydrophobic surfaces have regions displaying advancing contact angles for water greater than approximately one hundred and ten (110) degrees, in another embodiment, hydrophobic surfaces have regions displaying receding contact angles for water greater than approximately 100 degrees. It is important to note that some liquids, and particularly some biological liquids, contain elements that may coat a surface after wetting it, thereby affecting its hydrophobicity. In the context of the present invention, it may be important that a surface resists such coating from a liquid of intended use, for example, that such coating does not create an advancing and/or receding contact angle that is less than 90 degrees over the duration that the surface remains wetted by the said liquid.

A surface or a region on a surface is "hydrophilic" when it displays (e.g. advancing) contact angles for water less than approximately ninety (90) degrees, and more commonly less than approximately seventy (70) degrees (in many cases it is preferable that both the advancing and receding contact angles are less than approximately 90 degrees or approximately 70 degrees).

Measured contact angles can fall in a range, i.e. from the so-called advancing (maximal) contact angle to the receding (minimal) contact angle. The equilibrium contact is within those values, and can be calculated from them.

Hydrophobic surfaces "resist wetting" by aqueous liquids. A material is said to resist wetting by a first liquid where the contact angle formed by the first liquid on the material is greater than 90 degrees. Surfaces can resist, wetting by aqueous liquids and non-aqueous liquids, such as oils and fluorinated liquids. Some surfaces can resist wetting by both aqueous liquids and non-aqueous liquids. Hydrophobic behavior is generally observed by surfaces with critical surface tensions less than 35 dynes/cm. At first, the decrease in critical surface tension is associated with oleophilic behavior, i.e., the wetting of the surfaces by hydrocarbon oils. As the critical surface tensions decrease below 20 dynes/cm, the surfaces resist wetting by hydrocarbon oils and are considered oleophobic as well as hydrophobic.

Hydrophilic surfaces "promote wetting" by aqueous liquids. A material is said to promote wetting by a first liquid where the contact angle formed by the first liquid on the material is less than 90 degrees, and more commonly less than 70 degrees.

U.S. Pat. No. 8,647,861 [1], hereby incorporated by reference, describes microfluidic "organ-on-chip" devices comprising living cells on membranes in microchannels exposed to culture fluid at a flow rate. In contrast to static 2D culture, microchannels allow the perfusion of cell culture medium throughout the cell culture during in vitro studies and as such offer a more in vivo-like physical environment. In simple terms, an inlet port allows injection of cell culture medium into a cell-laden microfluidic channel or chamber, thus delivering nutrients and oxygen to cells. An outlet port then permits the exit of remaining medium as well as harmful metabolic by-products.

As used herein, the phrases "linked," "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

As used herein, the term "channels" are pathways (whether straight, curved, single, multiple, in a network, etc.) through a medium (e.g., silicon, plastic, etc.) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents.

As used herein, the term "Microchannels" is used to describe channels with dimensions less than 1 millimeter and greater than 1 micron. Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

The present invention contemplates a variety of "microfluidic devices," including but not limited to microfluidic chips (such as that shown in FIG. 1 and FIG. 2), perfusion manifold assemblies (without chips), and perfusion manifold assemblies engaged with microfluidic chips (such as that shown in FIG. 5). However, the methods described herein for engaging microfluidic devices (e.g. by drop-to-drop connections), and for perfusing microfluidic devices are not limited to the particular embodiments of microfluidic devices described herein, and may be applied generally to microfluidic devices, e.g. devices having one or more microchannels and ports.

As used herein, the term "masking" is used throughout to describe the application of a physical barrier upon a surface to prevent surface modification. Such a surface mask may be removed after unmasked surfaces have been modified, which results in a specific pattern of surface with varying surface characteristics.

As used herein, the term "pattern projection" is used throughout to describe the projection of a specific pattern of light upon a surface.

As used herein, the term "rastering" is used throughout to describe pattern of closely spaced rows of dots that form an image.

As used herein, the term "PEG" or "polyethylene glycol" is used to describe a polyether compound with a structure commonly expressed as H—(O—$CH_2$—$CH_2$)$_n$—OH.

As used herein, the term "TRIS" or "tris(hydroxymethyl)aminomethane" is used to describe a chemical with the formula ($HOCH_2$)$CNH_2$.

As used herein, the term "ANB-NOS" (N-5-azido-2-nitrobenzoyloxysuccinimide) is represented with the following structure

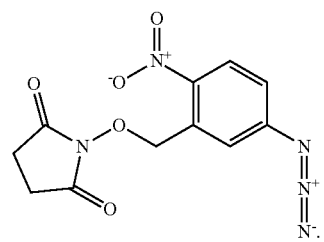

As used herein, the term "Sulfo-SAND" (sulfosuccinimidyl 2-[m-azido-o-nitrobenzamido]ethyl-1, 3-dithiopropionate) is represented with the following structure

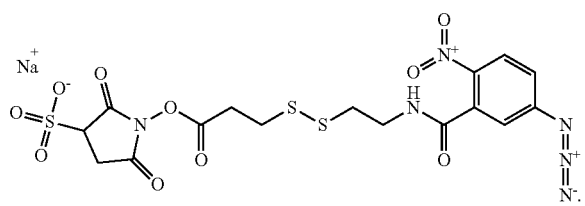

As used herein, the term "SAN PAH" (N-succinimidyl-6-[4-azido-2'-nitrophenylamino]hexanoate) is represented with the following structure

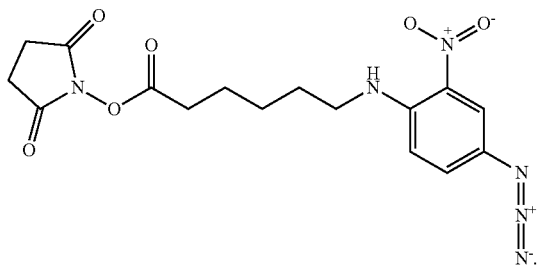

As used herein, the term "Sulfo-SANPAH" (sulfosuccinimidyl-6-[4'-azido-2'-nitrophenylamino]hexanoate) is represented with the following structure

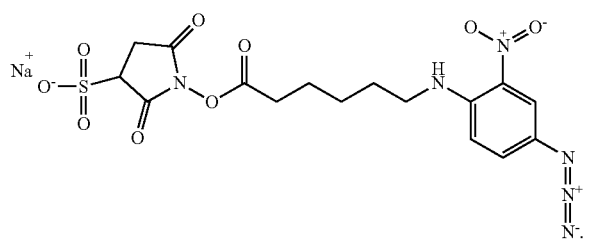

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating one or more embodiments of the invention and are not to be construed as limiting the invention.

FIG. 4A shows one embodiment of a fluidic backplane comprising serpentine fluid resistor channels (91), vacuum channels (92) and output channels (93). FIG. 4B is an edge view. FIG. 4C shows the chip engagement bosses (94) of the fluidic backplane, which serve as its fluidic outlet ports, along with assembly alignment features (95) and a visualization cutout (96) which permits microscopy and other imaging.

FIG. 11A-D shows a schematic of one embodiment of a drop-to-drop connection scheme whereby a combination of geometric shapes and surface treatments are used to control the droplet. FIG. 11A shows an embodiment of the microfluidic device or "chip" comprising a fluid channel and ports, having an elevated region at each port (e.g. a pedestal or gasket). When other portions of the device (i.e. portions other than the pedestal or gasket) are treated (e.g. sulfo-SANPAH or other crosslinker followed by light) to make them hydrophilic, the naturally hydrophobic pedestal or gasket can be protected with a mask (shown in FIG. 11A on top of the pedestal or gasket as element 41) during treatment to keep it from becoming hydrophilic. After treatment, the mask is removed (e.g. peeled off the surface of the pedestal or gasket). FIG. 11B shows the hydrophilic channel filled with fluid where the droplet radius is balanced at each end (i.e. at the port openings); the droplet (22) is constrained by the hydrophobic gasket surface. FIG. 11C shows one portion of the microfluidic device of FIG. 11B with an upward projecting droplet (22) approaching (but not yet in contact with) one portion of the mating surface of the perfusion manifold assembly, which also has a projecting droplet (in this case, the droplet (23) is projecting downward). FIG. 11D shows the same portion of the microfluidic device of FIG. 11C with the upward projecting droplet (22) of the microfluidic device making contact with (and merging with) the downwardly projecting droplet (23) of the perfusion manifold assembly (also called a pod). The droplets coalesce in a controlled manner when they are on hydrophilic surfaces but constrained by hydrophobic surfaces. As noted previously, embodiments where the microfluidic device approaches from above (with a downwardly projecting droplet) the perfusion manifold assembly (with an upwardly projecting droplet) are also contemplated.

DESCRIPTION OF THE INVENTION

This invention is in the field of surface modification. In particular, the invention relates to the surface modification of microfluidic devices to alter surface hydrophobicity characteristics.

In one embodiment, the invention contemplates the modification of surface hydrophobicity. In one embodiment, the invention contemplates the modification of surface hydrophobicity of materials involved in microfluidic systems. Microfluidics deals with the behavior, precise control and manipulation of fluids that are geometrically constrained to a small, typically sub-millimeter scale. It is a multidisciplinary field at the intersection of engineering, physics, chemistry, biochemistry, nanotechnology, and biotechnology, with practical applications in the design of systems in which low volumes of fluids are processed to achieve multiplexing, automation, and high-throughput screening. The behavior of fluids at the microscale can differ from "macrofluidic" behavior in that factors such as surface tension, energy dissipation, and fluidic resistance start to dominate the system. Modification of the surface hydrophobicity of materials in microfluidic systems may significantly alter a system's operation and character. In particular, modification of surface characteristics in microfluidic systems can enable one to further dictate the operation of the microenvironments. Further, specific patterning of surface modification, by way of masking, pattern projection or restoring for example, may provide an even greater measure of controlling the characteristics of a microfluidic system. Such modified surfaces may reduce bubble formation or introduction, discourage accumulation of protein, discourage cell growth, improve droplet formation, or provide further directional properties for the microenvironments.

Figure 7:
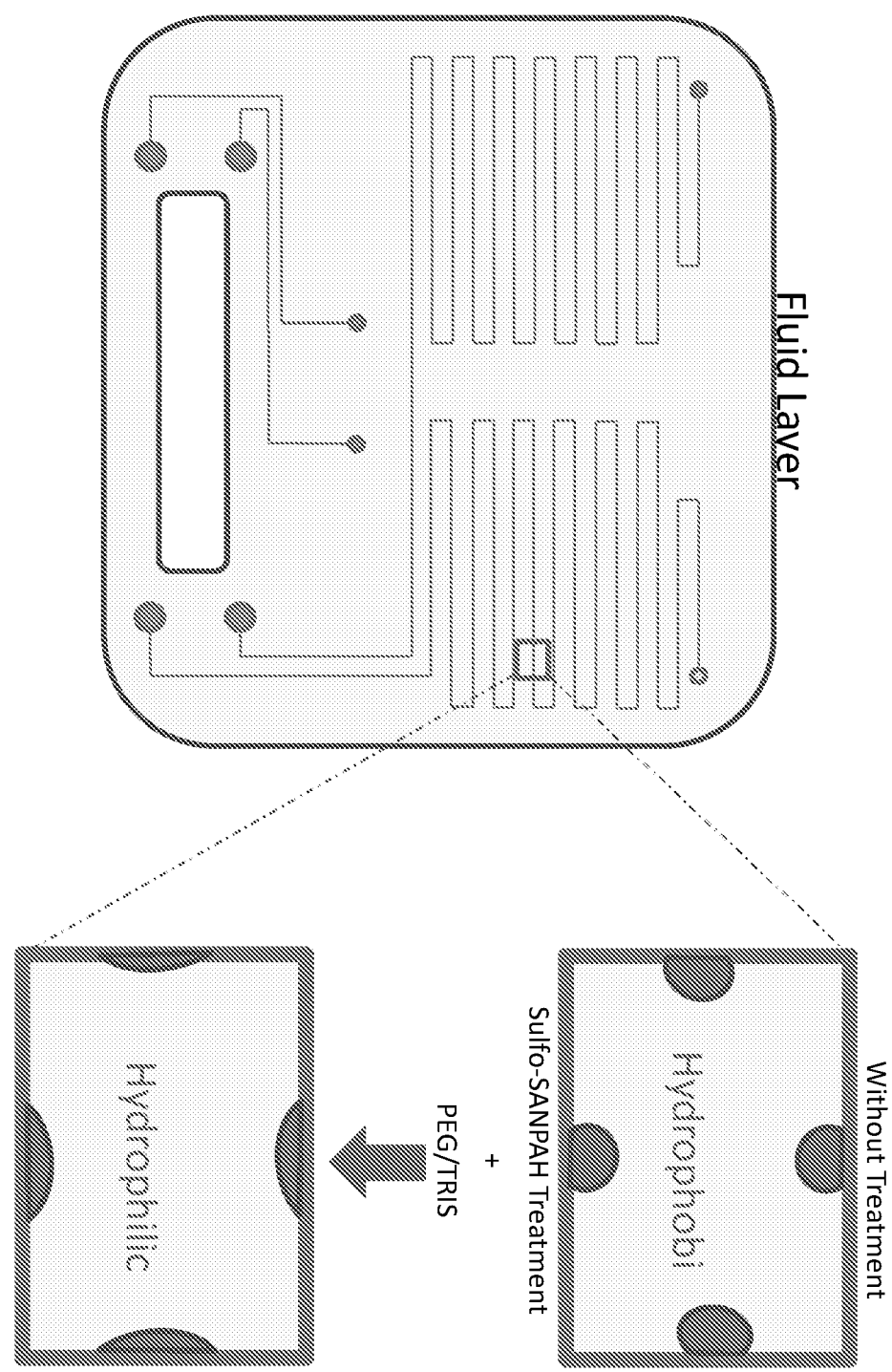
FIG. 7 shows a diagram of serpentine fluidic resistance channels within a microfluidic chip. The expanded insert illustrates how before treatment with sulfo-SANPAH with PEG/TRIS a droplet displays a large fluid contact angle indicating that the surface is hydrophobic and how after treatment it displays a small contact indicating that the surface is hydrophilic.

Bubbles inadvertently introduced into a microfluidic system can significantly and negatively affect device operation. If the bubble makes it into the growth area, poor cell viability can result. Bubbles are typically cytotoxic to the cells and will result in the rupturing of the cellular membrane due to desiccation. Moreover, bubbles can interfere with fluidic mixing and flow. As such, microfluidic systems are extremely sensitive to even a small bubble introduced into the device at any time. One approach to the bubble problem involves treating the surface in advance such that a bubble can more easily be moved out of the area. For example, bubbles trapped in the serpentine channels of a resistor, as in FIG. 7, can more easily be moved out of the resistor if the serpentine channels are first treated to make them more hydrophilic. Hydrophilic surface tend toward being wetted by water-liquid, while hydrophobic surfaces tend toward being dewetted by liquid and prefer contact with gas. This phenomena allows for bubbles (gas) to be dislodged and surfaces to be wetted with liquid more easily in the case of hydrophilic surface. Creating hydrophilic surface via the approach described herein is especially useful when the channel of interest is long and/or narrow as in FIG. 7, since alternative approaches for surface functionalization, like plasma-treatment and or chemical vapor deposition, are limited to a length of channel activation of less than 10 mm due to a reliance on passive diffusion of the activating molecule. In addition, these alternative methods tend not to be permanent, which is disadvantageous particularly in the case of Organ-Chips, where it is often necessary to culture under fluid flow for several weeks and long-term maintenance of surface characteristics are important for mitigating bubble effects for the duration of the experiment. Additionally, these coatings also tend to leach toxic components into the liquid they contact, either due to the coating itself degrading or washing off over time or due to secondary chemicals used in the coating process leaching into the fluid (e.g. organic solvents used to dissolve the coating before application, photo-initiators, or other harsh chemicals used as part of the coating process). Finally, it tends to be difficult to accurately control the location of activation in these alternative methods since activation will occur wherever depositions occurs, whereas in the method described here activation only occurs where photo-activated.

Priming is an important aspect in microfluidic systems which can significantly improve device operation. When a device surface is hydrophobic in character, there can be an impediment for the flow of aqueous medium through the device. The edge of an aqueous front must overcome greater barriers on a hydrophobic surface. This can interfere with the flow of the liquid and potentially lead to inconsistent or undesired paths of flow. One approach to the priming problem involves modifying the hydrophobic surface to be a more hydrophilic surface, the modified surface providing a lower barrier for priming of the fluid to move through an area. For example, aqueous liquid moving through the serpentine channels of a resistor can more easily move through the channels if they have been modified to provide a more hydrophilic surface. Another example is modifying the surface to facilitate drainage of liquid upon particular paths or to create hydrophobic and hydrophilic zones to facilitate flow and desired pathways. Such pathways are desired in certain embodiments of pod reservoirs.

The formation and distribution of droplets is an important aspect in microfluidics. The manipulation of discrete fluid packets in the form of microdroplets that provide numerous benefits for conducting biological and chemical assays. Among these benefits are a large reduction in the volume of reagent required for assays, the size of sample required, and the size of the equipment itself. Such technology also enhances the speed of biological and chemical assays by reducing the volumes over which processes such as heating, diffusion, and convective mixing occur. Once the droplets are generated, carefully designed droplet operations allow for the multiplexing of a large number of droplets to enable large-scale complex biological and chemical assays. Once formed, droplets must be kept in close contact for an amount of time, in order for fusion to occur. While not intending to limit the invention in any manner, fusion occurs due to fluctuations in the surface tension on the surface of droplets. One approach to droplet formation and manipulation involves modifying the hydrophobic character of the droplet forming surface to encourage directional droplet formation. For example, a port could be modified to have a hydrophilic surface on the inner surface, but a highly hydrophobic outer surface, which would encourage stable droplet formation: the droplet-surface static friction or "stiction" forces dominate over surface tension forces on the inner surface and the fluid will tend to wet the entire inner surface (with liquid), whereas surface tension dominates over fluid-surface stiction forces on the outer surface, which causes the outer surface to dewet. Together, this results in a spherical droplet that does not spread unpredictably across the outer surface, but is constrained to the fully-wetted inner surface. Another example would be the designing of a microfluidic device surface (such as a microchip or pod surface) which can be designed with hydrophilic and or hydrophobic regions to create stable droplets in desired regions, promoting better fluidic containment.

Another issue in microfluidic systems which involve interactions with living systems is the undesired deposition of cells, cellular debris, and related byproducts in areas of the microfluidic device which is undesired or reduces device performance. In such devices, there is usually a designated area of the device for cell or tissue growth. However, cells often take hold wherever they are able to make attachment. The characteristics of the unmodified surface of many microfluidic devices may provide a point of attachment beyond the desired area for growth. One approach to preventing undesired cell growth would be the modification of the surface. One example would be to modify certain device surfaces with polyethyleneglycol to prevent protein and cell attachment. Such a modification can protect fluid channels in chips, while effectively encouraging growth in the desired growth areas.

Current methods of functionalizing thermoplastic surfaces include plasma treating and corona treating. These methods are known for not being able to penetrate microfluidic channels depending on the size of the channel. In some embodiments, microfluidic device of the current invention comprise small microfluidic channels that act as a resistor and therefore cannot be treated using Plasma or a corona treater. The protocol of the current invention provides a method for treating these small channels and making it possible to bond reagents on to the surfaces. The present invention is not to be limited to any particular surface. In one embodiment, said surface comprises a microfluidic device. In one embodiment, said surface comprises a thermoplastic material. In one embodiment, said surface is selected from the group consisting of cyclo-olefin polymer (COP), polycarbonate (PC) and polydimethylsiloxane (PDMS). The present invention contemplates various approaches to modification of the hydrophobicity of a microfluidic surface. In one embodiment, the invention contemplates the use of crosslinking agents to covalently link to a surface, then covalently links to a hydrophilic or hydrophobic molecule. In such an approach the characteristics of the original surface have been modified to correspond with the new surface hydrophobicity modifying molecules. For example, a general approach to modification may include the following: 1) applying (e.g. wet or flow in) crosslinker solution into the desired surface area; 2) activation of the crosslinker (such as exposing with light of suitable wavelength and sufficient strength/exposure); 3) optionally wash (e.g. remove unreacted material); 4) applying the surface hydrophobicity modifying molecules (hydrophobic/hydrophilic material with suitable chemical group) to the crosslinked surface; 5) incubate to allow for reaction; 6) optionally wash (e.g. remove unreacted material). In one embodiment, the hydrophobicity modifying molecules are reacted with the crosslinker before activation of the crosslinker (such as exposure to light exposure). In this approach, a surface may be modified in one step and one application of the pre-combined crosslinker and hydrophobicity modifying molecules to a surface. In some embodiments, the invention contemplates selective application of surface modification. In one embodiment, the present method can be used to apply the surface modification in locations within a microfluidic device that are not directly accessible. For example, the present invention contemplates (in one embodiment) filling a channel (such as a serpentine channel of a resistor or a seeding channel) with bifunctional crosslinker and then shining light through the top (or the walls) of the channel, i.e. without opening the channel or the device. This could then be followed by functionalization by exposure to hydrophobicity modifying molecules, such as PEG or TRIS, by filling the device so the internal surfaces can be functionalized. In one embodiment, the present method can be used to apply the surface modification in defined locations by either only applying the modifying material to the selected area (e.g. only wetting some parts) or by only providing the crosslinker activation to the selected areas (e.g. by masking, pattern projection or rastering). In one embodiment, such selective application of surface modification or selective patterning contemplates the creation of a specific pattern of hydrophobic and/or hydrophilic surfaces. Such a pattern may enable control at interfaces or to stabilize droplets. In one embodiment, selective patterning may further delineate surface characteristics to control behavior in a system, such as preventing: cell attachment, accumulation of undesired molecules, bubble formation, etc. In one embodiment, selective patterning may further delineate surface characteristics to encourage behavior in a system, such as cell attachment, accumulation of desired molecules, droplet formation, etc. In one embodiment, the invention contemplates methods and compositions that functionalize the surface of thermoplastics and hydrophobicity modifying molecules (such as TRIS and PEG) to make the surface more hydrophilic. Making microfluidic channels hydrophilic reduces the amount a nucleation points that would normally trap air and cause bubbles.

The present invention is not to be limited to any particular crosslinker. In one embodiment, the crosslinkers of the current invention comprise three parts: a light-reactive portion, a linker, and a modifier-reactive portion. Such bi functional crosslinkers can be represented by the formula A-B-C, wherein A represents light-reactive portion, B represents a linker, and C represents modifier-reactive portion.

DESCRIPTION OF PREFERRED EMBODIMENTS

Crosslinkers

Figure 12:
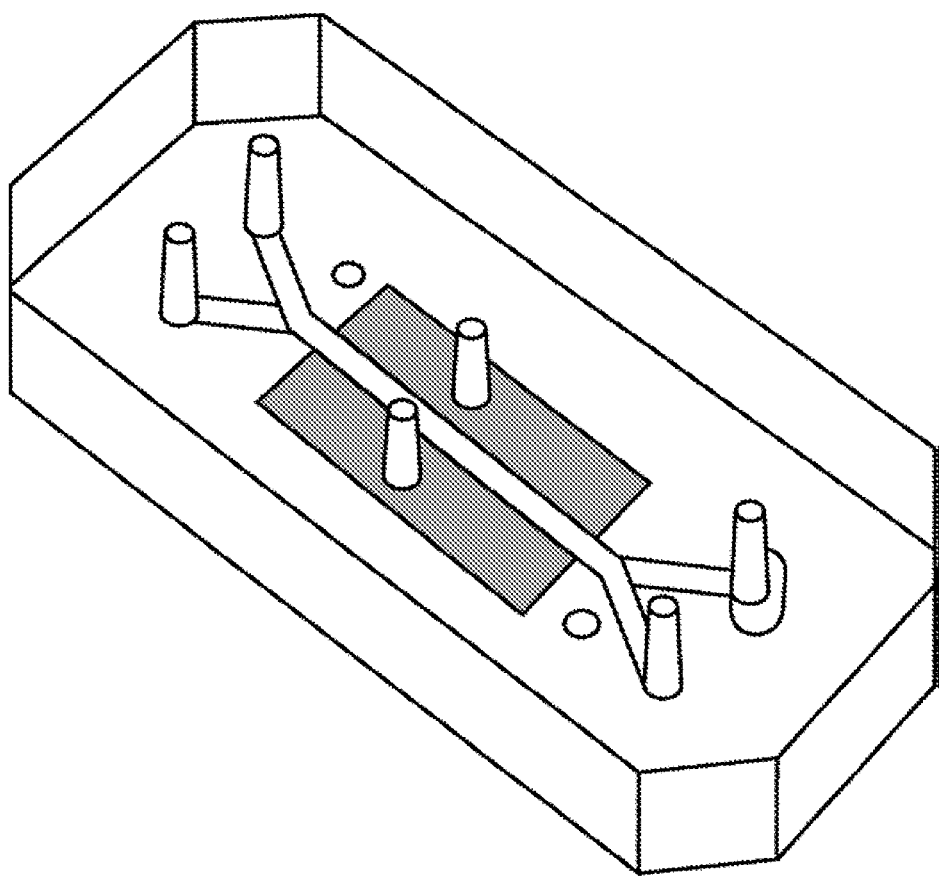
FIG. 12 shows an illustration of one embodiment of a microchip with a central channel for cell and two seeding channels on each end which flow into the central channel. In one embodiment, it is desired that cells will grow in the central channel, shown within the central shaded rectangle. In one embodiment, the seeding channels are treated to modify seeding channel surface hydrophobicity to prevent cell seeding/attachment or protein attachment in areas other than the central channel. In one embodiment, the end channels are crosslinked to PEG, which prevents attachment of cells and proteins. In one embodiment, this will enable proper functioning of the microchip and encourage cell growth in the central channel.
Figure 13:
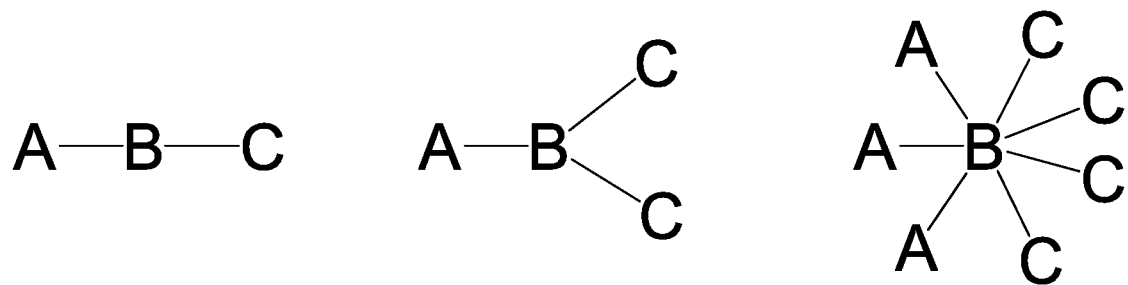
FIG. 13 shows generic examples of potential crosslinkers with the formula A-B-C, wherein A represents light-reactive portion, B represents a linker, and C represents modifier-reactive portion. The formula on the left represents a linear crosslinker, the formula in the center and the left represent where the liker portion is multivalent.
Figure 14:
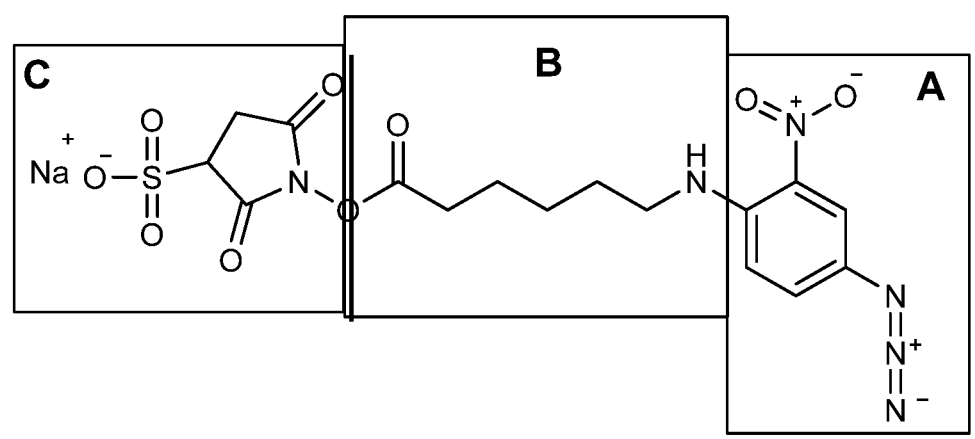
FIG. 14 shows a specific example of a crosslinker, Sulfo-SANPAH which is diagrammed according to the A-B-C crosslinker formula described above.

The present invention is not to be limited to any particular crosslinker. In one embodiment, the crosslinkers of the current invention comprise three parts: a light-reactive portion, a linker, and a modifier-reactive portion. In one embodiment, the hi functional crosslinkers are represented by the formula A-B-C, wherein A represents light-reactive portion, B represents a linker, and C represents modifier-reactive portion. The present invention is not to be limited to linear crosslinkers. In one embodiment, B can also be branched it multivalent. i.e. it can link one A to two Cs, 3As to 4Cs, etc, see FIG. 12. As a non-limiting example, sulfo-SANPAH uses a nitrophenyl azide group as the sight-reactive portion, aminohexanoate as the linker, and sulfo-NHS ester as the modifier-reactive portion (in this case reacting with an amine group on the modifier), see FIG. 13. In one embodiment, light reactive portions may be selected from the group consisting of nitrophenyl, diazirine, and azides. The present invention is not to be limited to any particular linker. In one embodiment, the linker (B) are connected to light-reactive portion (A) through an amine bond and modifier-reactive portion (C) through an ester bond. In one embodiment, the linkers may be selected from the group consisting of polyethyleneglycols, disulfides, alkanes, and olefins. In one embodiment, the modifier-reactive chemistry portion may be selected from the group consisting of NHS-ester (amine reactive), Sulfo-NHS-ester (amine reactive), Isocyanate (amine reactive), Isothiocyanate (amine reactive), Imidoester (amine reactive), Maleimide (sulfhydryl reactive), Pyridyldithiol (sulfhydryl reactive), and Hydrazide (aldehyde and ketone reactive). Specific examples of commercially available crosslinkers that fit this description include ANB-NOS, SDA, sulfo-SDA, LC-SDA, sulfo-LC-SDA, SDAD, sulfo-SDAD, and more (see Table 1). ANB-NOS is a short-arm (7.7 angstrom) crosslinker that contains an amine-reactive N-hydroxysuccinimide (NHS) ester and a photoactivatable nitrophenyl azide, also called N-5-azido-2-nitrobenzoyloxysuccinimide. Sulfo-SANPAH is a long-arm (18.2 angstrom) crosslinker that contains an amine-reactive N-hydroxysuccinimide (NHS) ester and a photoactivatable nitrophenyl azide, also called sulfosuccinimidyl 6-(4'-azido-2'-nitrophenylamino) hexanoate. SDA (NHS-Diazirine) combines proven NHS-ester and diazirine-based photoreaction chemistries with conjugate amine-containing molecules with nearly any other functional group via long-wave UV-light activation. SDA (Sulfo-NHS-Diazirine) is an amine and photoreactive, membrane impermeable, heterobifunctional crosslinker with a 3.9 Angstrom spacer arm. Also called Sulfosuccinimidyl 4,4'-azipentanoate. LC-SDA (NHS-LC-Diazirine) is an amine and photoreactive, membrane permeable, heterobifunctional crosslinker with a 12.5 Angstrom spacer arm. Also called Succinimidyl 6-(4,4'-azipentanamido)hexanoate. Sulfo-LC-SDA (Sulfo-NHS-LC-Diazirine) is a sulfo-NHS-diazirine based photoreactive crosslinker. Membrane impermeable with a 12.5 Angstrom spacer arm. Also called Sulfosuccinimidyl 6-(4,4'-azipentanamido)hexanoate.

TABLE 1

Examples of commercially available crosslinkers

| Reactive Groups | Products | Spacer Arm (Å) | | Cleavable by? | Water-soluble? | Membrane permeable? |
|---|---|---|---|---|---|---|
| NHS ester/ aryl azide | ANB-NOS | 7.7 | Short | No | No | No |
| | Sulfo-SANPAH | 18.2 | Long | No | Yes | No |
| NHS ester/ diazirine | SDA | 3.9 | Short | No | No | Yes |
| | Sulfo-SDA | 3.9 | Short | No | Yes | No |
| | LC-SDA | 12.5 | Mid | No | No | Yes |
| | Sulfo-LC-SDA | 12.5 | Mid | No | Yes | No |
| | SDAD | 13.5 | Mid | Thiols | No | Yes |
| | Sulfo-SDAD | 13.5 | Mid | Thiols | Yes | No |

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups (—$NH_2$) in pH 7-9 buffers to form stable amide bonds. The reaction results in the release of N-hydroxy-succsnimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using a second filter that removes wavelengths above 370 nm could be beneficial but is not essential.

Hydrophobicity Modifying Molecules

The present invention is not to be limited to any particular surface hydrophobicity modifying molecules. For example a crosslinker, described above, may covalently link to a hydrophilic or hydrophobic molecule. Non-limiting examples of hydrophilic molecules include PEG (and various derivatives), tris(hydroxymethyl)aminomethane (TRIS), poly vinyl alcohol, poly(lactic acid) (PLA). In one embodiment, PEG may be used to repel proteins and cells. Non-limiting examples of hydrophobic molecules: alkanes of various lengths, fluorocarbons, various fluorinated materials (PTFE, FEP, etc.), some nylons.

There are many instances wherein one would want to turn a surface hydrophilic or hydrophobic in microfluidic device applications. Specific non-limiting examples include: microfluidic device pod reservoirs: one may want the reservoir to have hydrophilic or hydrophobic surface characteristics (or even zones of each) to facilitate drainage of small liquid volumes; microfluidic device pod resistor: one may want the resistor to have a hydrophilic surface for better bubble clearance and easier priming, since less pressure will be required to wet the resistor in both applications due to the tendency of the surface to wet with liquid (the bubble will be dislodged as fluid wets the surface and the air will be removed from the channel as the fluid wets the channel surface); microfluidic device chip "seeding channels" to prevent cell attachment where it is not desired. This actually goes beyond hydrophilic: PEG is good at preventing proteins and cells from attaching; a property related to but distinct from it being hydrophilic. FIG. 11 shows an illustration of a microchip with a central channel for cell and two channels on each end which flow into the central channel. In one embodiment, it is desired that cells will grow in the central channel, shown within the central shaded rectangle. In one embodiment, the end channels are treated to modify channel surface hydrophobicity to prevent cell seeding/attachment or protein attachment in areas other than the central channel. In one embodiment, the end channels are crosslinked to PEG, which prevents attachment of cells and proteins. This will enable proper functioning of the microchip. Microfluidic device chip-to-pod interface: the microfluidic device chip and/or microfluidic device pod (perfusion manifold assembly) surfaces can be designed with hydrophilic and/or hydrophobic regions to create stable droplets, which promote bubble-free fluidic attachment as well as limit the loss of fluid volume due to unconstrained spread/wetting of the fluid on the surface.

Microfluidic Devices

It is not intended that the present invention be limited by the nature of the microfluidic device. However, preferred microfluidic devices are described in U.S. Pat. No. 8,647, 861 [1], hereby incorporated by reference, and they are microfluidic "organ-on-chip" devices comprising living cells in microchannels, e.g. cells on membranes in microchannel exposed to culture fluid at a flow rate. The surfaces of the microchannels and/or the membrane can be coated with cell adhesive molecules to support the attachment of cells and promote their organization into tissues. Where a membrane is used, tissues can form on the upper surface, the lower surface or both. In one embodiment, different cells are living on the upper and lower surfaces, thereby creating one or more tissue-tissue interfaces separated by the membrane. The membrane may be porous, flexible, elastic, or a combination thereof with pores large enough to only permit exchange of gases and small chemicals, or large enough to permit migration and transchannel passage of large proteins, as well as whole living cells. In one embodiment, the membrane can selectively expand and retract in response to pressure or mechanical forces, thereby further physiologically simulating the mechanical force of a living tissue-tissue interface.

There are various types of mircrofluidic systems. One such type of microfluidic system are microfluidic devices. In one embodiment, the present invention contemplates a variety of "microfluidic devices," including but not limited to microfluidic chips (such as that shown in FIG. 1 and FIG. 2), perfusion manifold assemblies (without chips), and perfusion manifold assemblies engaged with microfluidic chips (such as that shown in FIG. 5). However, the methods described herein for engaging microfluidic devices (e.g. by drop-to-drop connections), and for perfusing microfluidic devices are not limited to the particular embodiments of microfluidic devices described herein, and may be applied generally to microfluidic devices, e.g. devices having one or more microchannels and ports. The present invention contemplates in one embodiment "perfusion manifold assemblies" or "perfusion disposables," which facilitate the culture of Organs-on-Chips within a culture instrument. While the present invention contemplates "disposable" embodiments, the element may (alternatively) be reusable (e.g. as a cost consideration). In one embodiment, these perfusion disposables (PDs) include one or more input and one or more output reservoirs, as well as elements required for pumping. In particular, in our present embodiment perfusion disposables include one or more resistors (see FIG. 4A), which are used for pressure-driven pumping. In the pressure-driven embodiment, the instalment creates or controls fluid flow by applying a pneumatic pressure (whether positive or negative) to one or more of the reservoirs. One advantage of this approach is that the pressure-driven design can avoid liquid contact with the instrument, which offers benefits in terms of sterility and ease of use (e.g. avoiding gas bubbles in liquid lines). In one embodiment, said resistor comprises serpentine channels. In one embodiment, said fluidic backplane is made of Cyclo Olefin Polymer (COP) (such as Zeonor 1420R, which is commercially available) and comprises linear fluid channels in fluidic communication with said serpentine channels, said linear channels terminating at one or more ports. In some embodiments, the instrument applies pressure directly to the one or more reservoirs (with no lid). A sufficient pressure seal may be attained by integrated one or more gaskets on the perfusions disposable and or the instrument (for example, as part of a pressure manifold). However, it is desirable that when the perfusion disposables are outside of the instrument the reservoirs are protected from contamination, for example, from environmental particles or airborne microbes. Accordingly, in the same embodiments it may be desirable to provide a lid that a user can employ to cover the reservoir.

Figure 1:
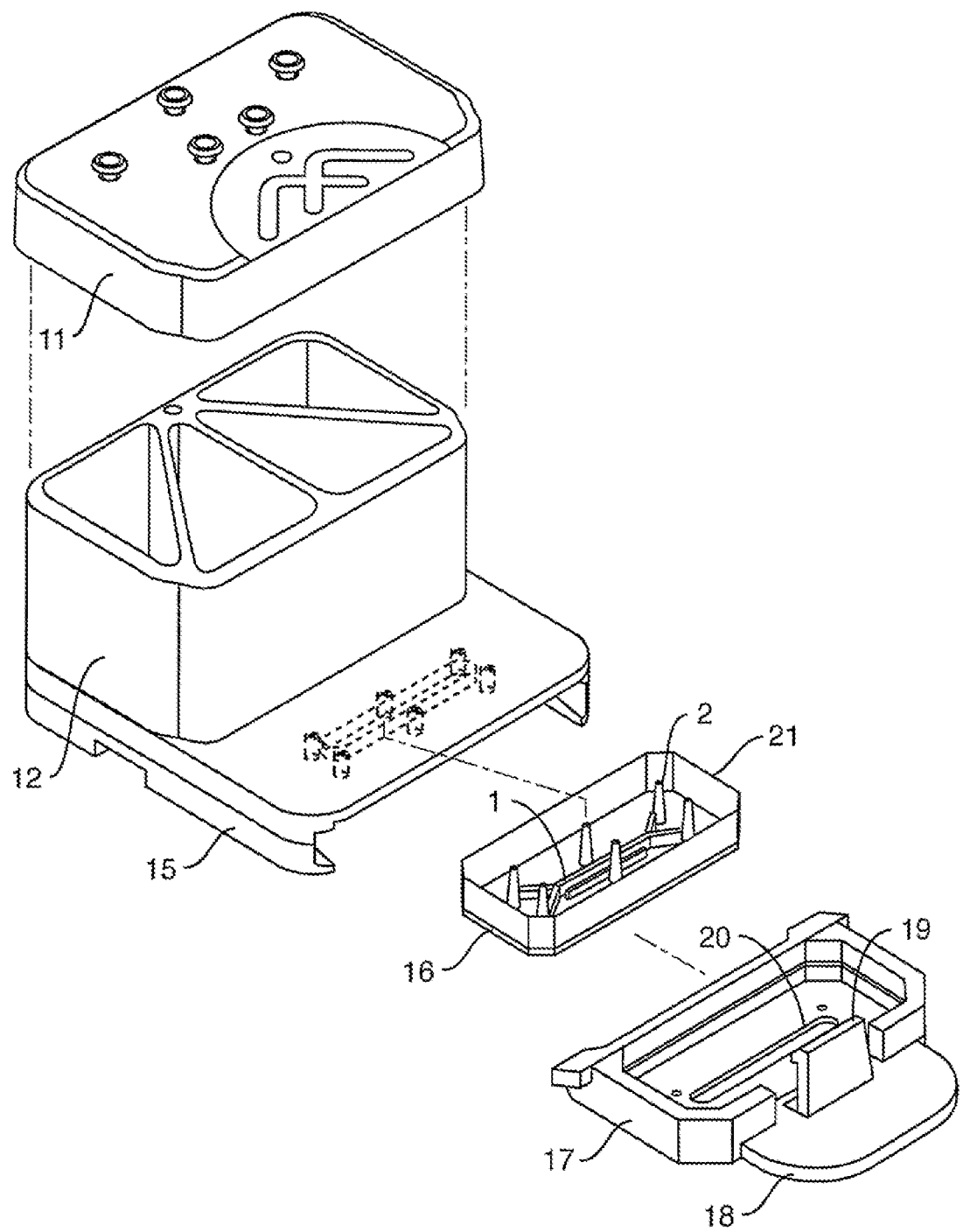
FIG. 1 is an exploded view of one embodiment of the perfusion manifold assembly showing the cover (or cover assembly) off of the reservoirs (the reservoir body can be made of acrylic, for example), the reservoirs positioned above the backplane, the backplane in fluidic communication with the reservoirs, the skirt with a side track for engaging a representative microfluidic device or "chip" (which can be fabricated out of plastic, such as PDMS, for example) having one or more inlet, outlet and (optional) vacuum ports, and one or more microchannels, the chip shown next to (but not in) one embodiment of a chip carrier (which can be fabricated out of a thermoplastic polymer, such as acrylonitrile butadiene styrene (ABS), for example), the carrier being configured to support and carrier the chip, e.g. dimensioned so that the chip fits within a cavity.
Figure 2:
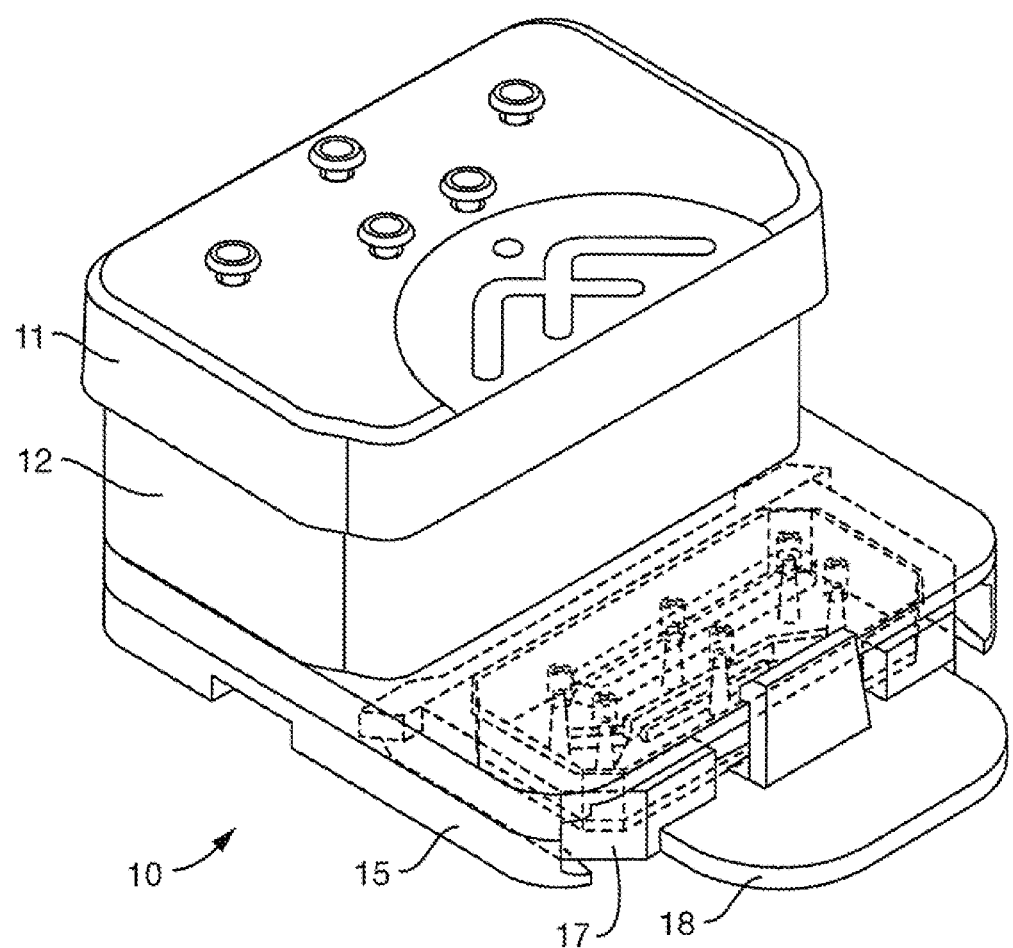
FIG. 2 shows the same embodiment of the perfusion manifold assembly with the cover on and over the reservoirs, and the chip inside the chip carrier fully linked to the skirt of the perfusion manifold assembly, and thereby in fluidic communication with the reservoirs. In one embodiment, each chip has two inputs, two outputs and (optionally) two connections for the vacuum stretch. In one embodiment, putting the chip in fluidic communication connects all six in one action, rather than connecting them one at a time.
Figure 3:
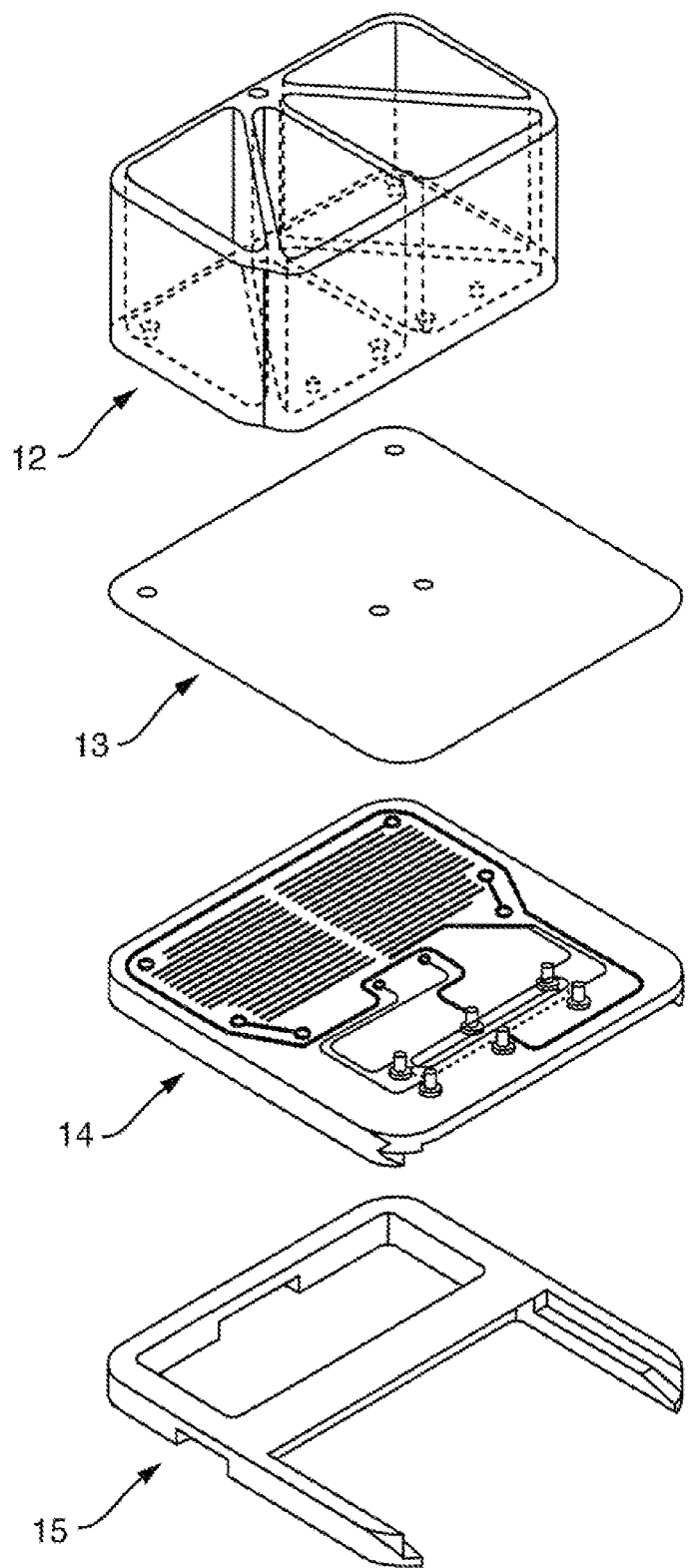
FIG. 3 is an exploded view of one embodiment of the perfusion manifold assembly (before the components have been assembled) comprising reservoirs positioned over a fluidic backplane (comprising a fluid resistor), that is fluidically sealed with a capping layer and is positioned over a skirt, with each piece dimensioned to fit over the next. In one embodiment, the skirt comprises structure (e.g. made of polymer) that borders or defines two open spaces, one of the spaces configured to receive the carrier with the chip inside. In one embodiment, the skirt has structure that completely surrounds one open space and two "arms" that extend outwardly that define a second open space for receiving the carrier. In one embodiment, the two arms have side tracks for slidably engaging the carrier edges.
Figure 4:
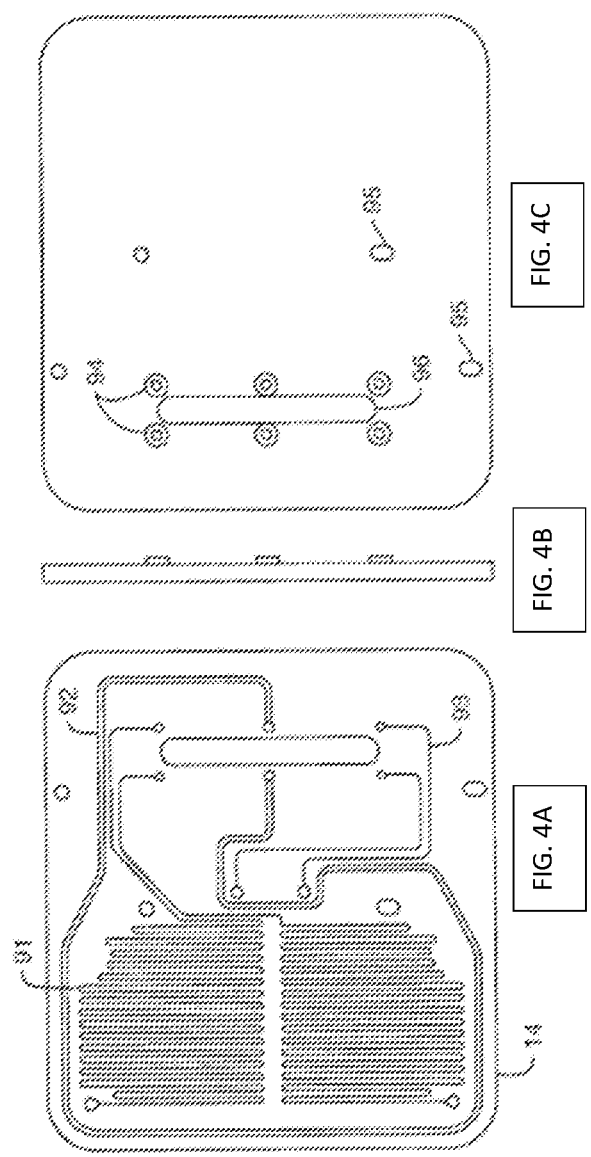
FIG. 4A-C show various views of one embodiment of the device.

In one embodiment (as shown in FIGS. 1, 2 and 3), the perfusion manifold assembly (10) comprises i) a cover or lid (11) configured to serve as to top of ii) one or more fluid reservoirs (12), iii) a capping layer (13) under said fluid reservoirs), iv) a fluidic backplane (14) under, and in fluidic communication with, said fluid reservoirs), said fluidic backplane comprising a fluidic resistor, and v) a projecting member or skirt (15) for engaging the microfluidic device (16) or chip which is preferably positioned in a carrier (17), the chip having one or more microchannels (1) and in fluidic communication with one or more ports (2). The assembly can be used with or without the lid or cover. Other embodiments (discussed below) lack a skirt or projecting member. In one embodiment, the carrier (17) has a tab or other gripping platform (18), a retention mechanism such as a clip (19), and a visualization cutout (20) for imaging the chip. The cutout (20) can enable placing a carrier (e.g. a carrier engaged with the perfusion manifold assembly or "pod" or not so engaged) onto a microscope or other inspection device, allowing the chips to be observed without having to remove the chip from the carrier. In one embodiment, the fluidic resistor comprises a series of switchbacks or serpentine fluid channels. FIG. 4A-C shows an enhanced schematic of one embodiment of the backplane, showing the fluid resistor channels (FIG. 4A) and chip engagement bosses FIG. 4C) or ports. A variety of fluid resistors designs are contemplated, as described more fully in U.S. Provisional Application Ser. Nos. 62/024,361 and 62/427,438, which became PCT/US2015/040026 [2], hereby incorporated by reference (and in particular, the discussion of resistors, resistor design, and pressures is incorporated herein by reference). In one embodiment, the perfusion manifold assembly is made of plastic and is disposable, i.e. it is disposed of after docking with and perfusing a microfluidic device. While the present invention contemplates "disposable" embodiments, the element may (alternatively) be reusable (e.g. as a cost consideration).

In one embodiment, the microfluidic device (e.g. chip) (16) may first be placed in a carrier (17) (e.g. chip carrier) before engaging the perfusion manifold assembly (10) or may engage the assembly directly. In either case, the (optional) detachable linking of the microfluidic device with the manifold should either a) prevent air from entering the microchannels, or b) provide a way for undesirable air to be removed or vented out of the system, indeed, air removal may be needed in some embodiments during both chip attachment and use of the microfluidic device.

Figure 5:
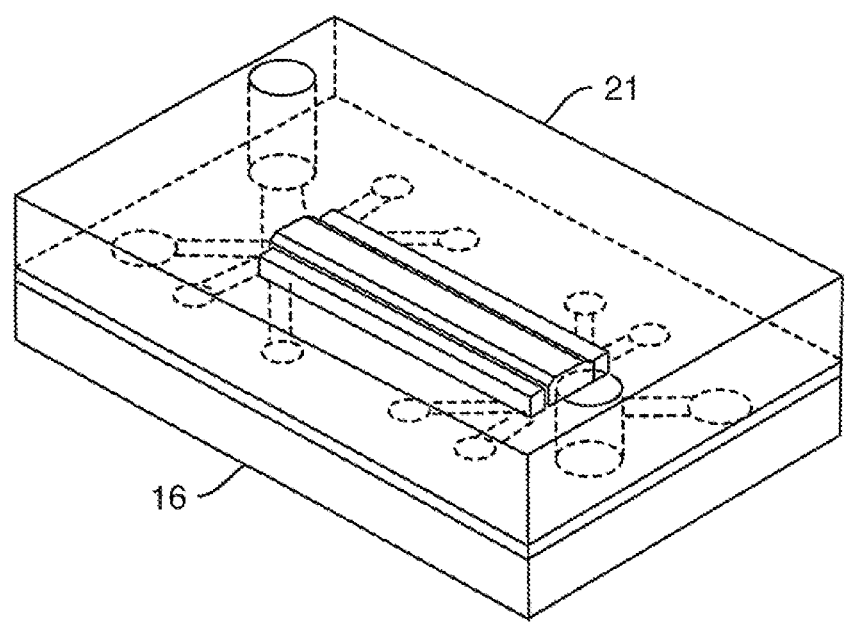
FIG. 5 shows a schematic of an illustrative microfluidic device or "organ-on-chip" device. The assembled device is schematically shown in FIG. 5.
Figure 6:
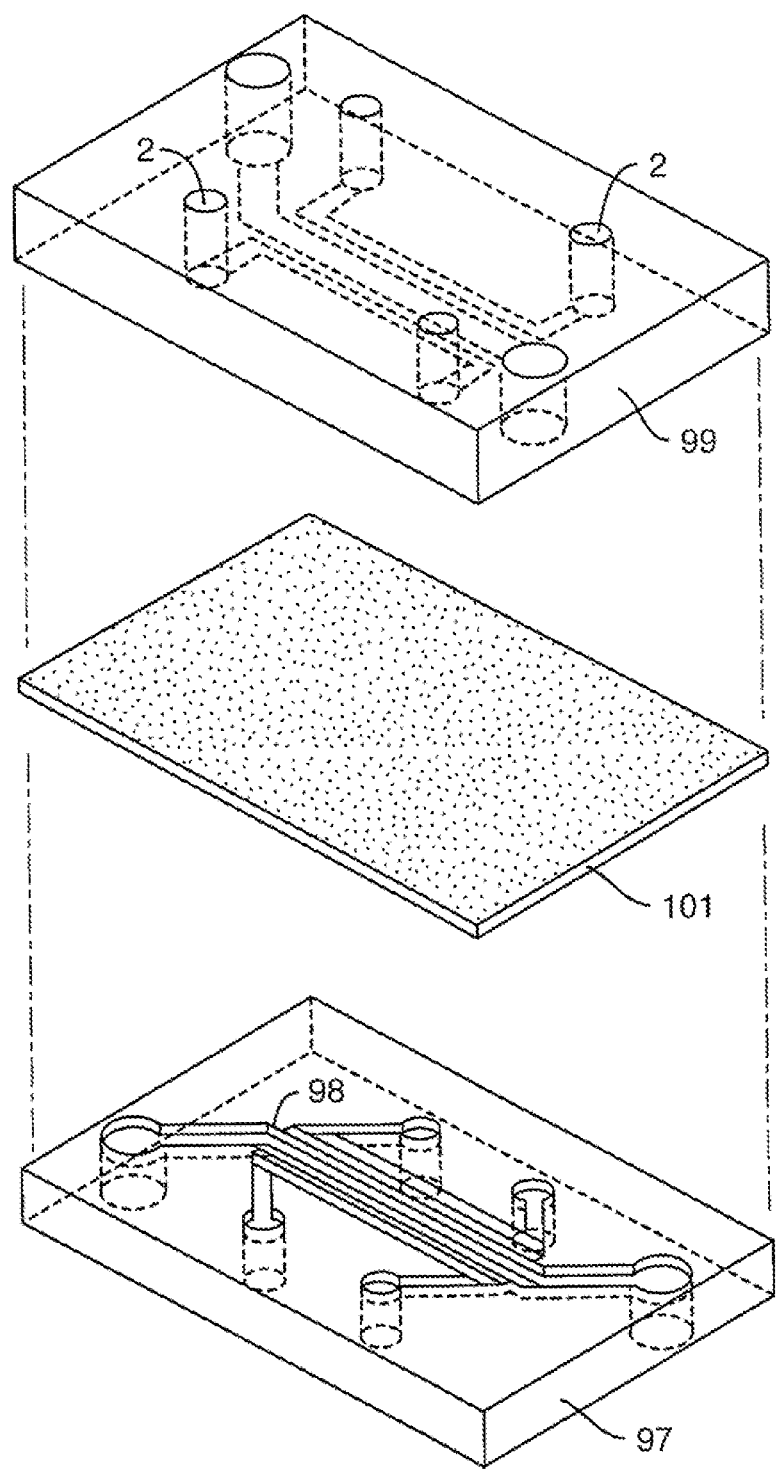
FIG. 6 shows an exploded view of the device of FIG. 5.

By way of example, FIG. 5 shows a schematic of an illustrative microfluidic device or "organ-on-chip" device. The assembled device is schematically shown in FIG. 5, which includes a plurality of ports. FIG. 6 shows an exploded view of the device of FIG. 5, showing a bottom piece (97) having channels (98) in a parallel configuration, and a top piece (99) with a plurality of ports (2), with a tissue-tissue interface simulation region comprising a membrane (101) between the top (99) and bottom (97) pieces, where cell behavior and or passage of gases, chemicals, molecules, particulates and cells are monitored. In an embodiment, an inlet fluid port and an outlet fluid port are in communication with the first central microchannel such that fluid can dynamically travel from the inlet fluid port to the outlet fluid port via the first central microchannel, independently of the second central microchannel. It is also contemplated that the fluid passing between the inlet and outlet fluid ports may be shared between the central microchannels. In either embodiment, characteristics of the fluid flow, such as flow rate and the like, passing through the first central microchannel is controllable independently of fluid flow characteristics through the second central microchannel and vice versa.

Anti-Fouling Treatments

Non-specific accumulation of biological matter at surfaces (also called "fouling") is to be avoided, particularly with microfluidic devices. Although sometimes fouling of surfaces with biomolecules has little consequence, bio fouling with microfluidic devices must be minimized or controlled in order to maintain performance, particular where cell culture is involved. For example, where cells in a microfluidic device are exposed to the flow of a biofluid, components in the biofluid such as proteins, other cells and the like have a propensity to strongly adhere to surfaces, altering performance with potential negative effects on cell viability. In one embodiment, the present invention contemplates inhibiting, preventing and/or limiting biofouling of surfaces using grafted molecules, including strategies for linking polymers onto polymer surfaces.

Prior methods for avoiding fouling are difficult because they either don't penetrate well into the depth of channels (e.g. plasma, chemical vapor deposition), or they don't last long (e.g. they are adsorbed coatings that tend to wash off). Moreover, prior methods often do not allow one to select the location for surface treatment (e.g. since they aren't photo-activated), and can leave toxic remains or residues (e.g. because they require organic solvents, photo-initiators, harsh chemicals, etc.).

In one embodiment, the present invention contemplates preventing, inhibiting and or limiting biofouling where an anti-fouling polymer is "grafted" onto a surface, including but not limited to a surface of a microfluidic device. One of the most studied anti-fouling polymers is poly(ethylene glycol) (PEG), a water soluble polymer with low toxicity. PEG is widely available commercially. Polymers like PEG can be grafted onto surfaces to reduce the nonspecific adsorption of proteins, cells and the like.

In one embodiment, the present invention contemplates in-situ polymerization of the non-fouling polymer (e.g. PEG) from a grafted initiator. However, in a preferred embodiment, the present invention contemplates grafting of anti-fouling polymers onto surfaces using the (complete) synthesized polymer via a chemical anchoring group.

Microfluidic devices are often made of PDMS, in spite of the well-known fouling properties of this polymer. In one embodiment, the present invention contemplates an anti-fouling method comprising 1) attaching a bifunctional crosslinker to the PDMS, or other polymer, itself (without the need for pretreatment of the PDMS to create free amine groups or the like) to create a bound crosslinker, and 2) attaching a non-fouling polymer, such as PEG, to the bound crosslinker. In a preferred embodiment, the bifunctional crosslinker is photoactivatable, e.g. Sulfo-SanPAH and others mentioned above.

Unlike prior methods for avoiding fouling, the presently contemplated penetrate well into the depth of channels (e.g. microchannels of microfluidic devices) and they last (i.e. since they are covalent attachments, they do not wash off.

Moreover, use of a photoactivatable bifunctional crosslinker allows one to select the location for surface treatment (e.g. since one can control where light comes in contact and thus when they are photo-activated). Finally, PEG and the like are non-toxic and the process docs not require harsh chemicals.

Anti-Clotting

A current challenge in microfluidic devices is ability to flow whole blood without getting clotting. Blood clotting can be caused by cell activation as blood passes through rough microfluidic channel surfaces, particularly when the microfluidic devices are fabricated using thermoplastic materials. The present invention contemplates, in one embodiment, a method to prevent (or at least inhibit) clotting of blood in thermoplastic chips by covalently bonding anticoagulants to the surfaces of the chip channels using crosslinkers, and in particular, bifunctional crosslinkers that are photoactivatable, such as Sulfo-SanPAH.

As noted above, a bifunctional crosslinker can bind a surface directly (on one end of the crosslinker) and then bind an anticoagulant (on the other end). For example, Sulfo-Sanpah contains a amine-reactive ester that can be used to bind amine containing anticoagulants to the thermoplastic surfaces. Some examples of anticoagulants that contain amine groups are: Heparin, Rivaroxaban (secondary amine), Dabigatran (secondary amine), apixaban (primary amine), edoxaban (secondary amine), fondaparinux (secondary amine) and enoxaparin (secondary amine). While not intending to limit the invention to any particular mechanism, the bond should theoretically be most efficient with apixaban because it contains a free primary amine.

EXAMPLES

The following examples are provided in order to demonstrate and further illustrate certain preferred embodiments and aspects of the present invention and are not to be construed as limiting the scope thereof.

Example 1

General Process for One Embodiment of the Method 1) wet (e.g. flow in) crosslinker solution into the desired area
2) expose with light of suitable wavelength and sufficient strength/exposure
3) optionally wash (e.g. remove unreacted material)
4) wet (e.g. flow in) hydrophobic/hydrophilic material with suitable chemical group
5) incubate to allow for reaction
6) optionally wash (e.g. remove unreacted material)

(See Example 2 for a specific protocol. See EXAMPLE 5 or Example 6 for an alternative process).

Example 2

Surface Functionalization of Thermoplastics Using Sulfo-Sanpah

One embodiment of the surface functionalization process is described below:
1. Take SS and make a 1 ml mg concentration using 50 mM Hepes.
2. Apply SS on the surface of the COP (enough to completely cover surface).
3. Place COP in UV Chamber and treat for 20 minutes.

Figure 8:
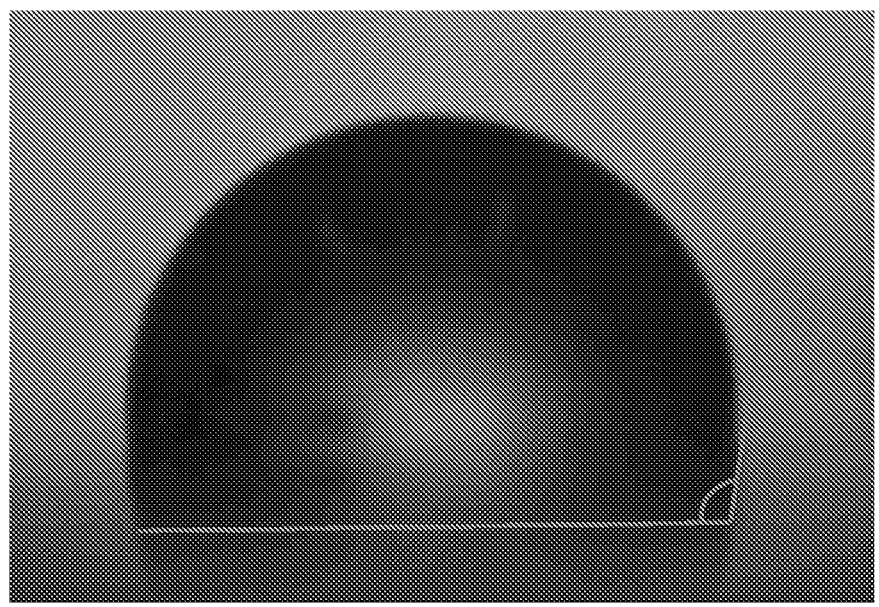
FIG. 8 shows a droplet on an untreated COP, which displays a large contact angle indicating that the surface is hydrophobic.
Figure 9:
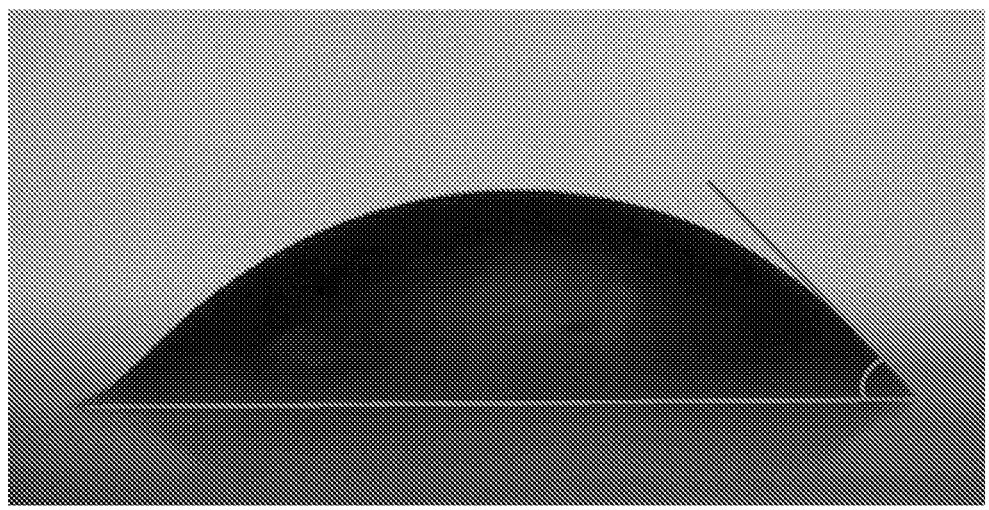
FIG. 9 shows a droplet on sulfo-SANPAH+TRIS treatment COP, which displays a much smaller contact angle indicating that the surface is hydrophilic.
Figure 10:
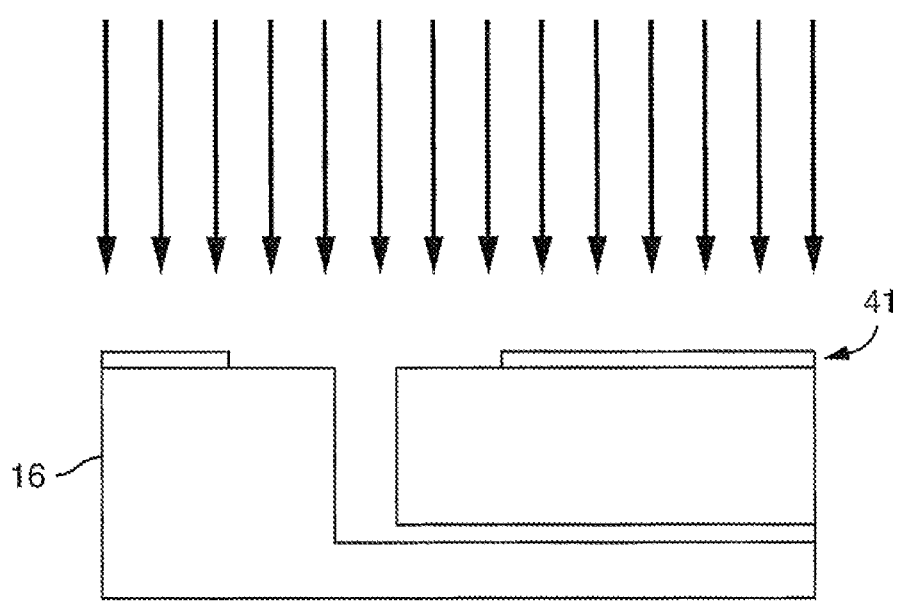
FIG. 10 shows a schematic showing a surface modification embodiment employing surface treatment (e.g. sulfo-SANPAH or other crosslinker followed by light, which indicated by downward projecting arrows) in conjunction with a mask (41); in one embodiment, the microfluidic device (16) is made of a naturally hydrophobic material which becomes hydrophilic upon such surface treatment where there is no mask, but remains hydrophobic where there is a mask. After the surface treatment, the mask can be removed and the channel can be filled with fluid so as to generate a droplet protruding above the surface, but constrained by the regions that remained hydrophobic.

4. Aspirate SS and wash with 50 mM Hepes.
5. Repeat steps 1-4.
6. Apply TRIS on the surface of the COP (enough to completely cover surface).
7. Leave COP overnight at 4° C.
8. Aspirate excess TRIS, result is COP coated with PEG or TRIS Different parameters were also tested, such as higher concentrations of SS, longer treatment times, and multiple treatments. This protocol was tested using TRIS, but may also be used with any amine containing buffer. The methods above yielded the best result when measuring the water contact angle of the COP after treatment. See FIG. 8, which shows a droplet on an untreated COP, which displays a large contact angle indicating that the surface is hydrophobic. FIG. 9 shows a droplet on sulfo-SANPAH+TRIS treatment COP, which displays a much smaller contact angle indicating that the surface is hydrophilic.

Example 3

Surface Functionalization

In one embodiment, in order to bond with Sulfo-SANPAH in particular, any of the hydrophobicity modifying molecules need to include (or be modified to include) amine, as that is what SANPAH binds. For example, to bind PEG, we used amine-terminated PEG, e.g. Poly(ethylene glycol) 2-aminoethyl ether acetic acid or HO-PEG$_{20K}$-NH$_2$. Alternative crosslinkers can have other reactive groups, requiring the hydrophilic or hydrophobic material to provide a different functional group to react with the crosslinker.

Example 4

Surface Functionalization of Thermoplastics Using Sulfo-Sanpah Conditions Tested In one embodiment, the materials were tested on open surfaces with a SEBS ring over the material to make a well, after the treatment the SEBS ring was removed so that the area that was treated could be isolated and compared to an untreated area of the same material.

TABLE 2

Conditions Tested

| Entry | Conditions | Material: | Results: |
|---|---|---|---|
| 1 | 20 minutes UV exposure Sulpho-SANPAH | SEBS | No Effect |
| 2 | 20 minutes UV exposure Sulpho-SANPAH | COP | Improves wetting |
| 3 | 30 minutes UV exposure with Sulpho-SANPAH | SEBS | No Effect |
| 4 | 30 minutes UV exposure with Sulpho-SANPAH | COP | No Effect (Note: Caused surrounding SEBS ring to bond to COP) |
| 5 | 20 minute UV exposure with Sulpho-SANPAH (x 2) | SEBS | No Effect |
| 6 | 20 minute UV exposure with Sulpho-SANPAH (x 2) | COP | Improves wetting (best condition) |

The forth entry had no effect in terms of making the material hydrophilic, but it had an interesting side effect us the SEBS ring was bonded to the COP material and could not be removed (perhaps a new discovery of using Sulfo-Sanpah to bond COP & SEBS). The best result in terms how showing hydrophilic properties was when the treatment was performed twice, it is important to note that this protocol can be further optimized.

Example 5

Alternative Crosslinker Functionalization

In one embodiment, optionally, the hydrophilic or hydrophobic chemical can be reacted with the sulfo-SANPAH before SS is bonded to the surface to be modified using light exposure. By doing this and providing the pre-reacted material to an end-user, the end-user only needs to perform a one-step process.

Example 6

Direct Surface Functionalization

In one embodiment, one can skip the crosslinker altogether and directly bind PEG (or other materials) to the surface. For example, O-(2-Aminoethyl)-O'-(2-azidoethyl) heptaethylene glycol uses the light-reactive chemistry. It should be possible to apply O-(2-Aminoethyl)-O'-(2-azidoethyl)heptaethylene glycol just as above except in a single step. (This may not be the best material for bonding to COP and PDMS, but one could have a nitrophenyl-PEG synthesized).

Example 7

Surface Functionalization of Thermoplastics Using Other Crosslinkers

Using the same method as for sulfo-SANPAH (as described in EXAMPLE 3 and EXAMPLE 4) but substituted sulfo-SDA (same protocol, same concentration, same exposure), but it was found that sulfo-SDA did not successfully graft to COP or SEBS.

| LIST OF REFERENCE NUMERALS | |
|---|---|
| Part | # |
| microchannels | 1 |
| port (e.g. a pedestal or gasket) | 2 |
| perfusion manifold assembly | 10 |
| cover or lid | 11 |
| fluid reservoirs | 12 |
| capping layer | 13 |
| fluidic backplane | 14 |
| projecting member or skirt | 15 |
| microfluidic device or chip BOTTOM | 16 |
| carrier | 17 |
| tab or other gripping platform | 18 |
| retention mechanism such as a clip | 19 |
| visualization cutout | 20 |
| microlluidic device or chip TOP | 21 |
| upward projecting droplet | 22 |
| downward projecting droplet | 23 |
| mask | 41 |
| serpentine fluid resistor channels | 91 |
| vacuum channels | 92 |
| output channels | 93 |
| chip engagement bosses | 94 |
| alignment features | 95 |
| visualization cutout | 96 |
| bottom piece | 97 |
| channels | 98 |
| top piece | 99 |
| membrane | 101 |

Thus, specific compositions and methods of surface functionalization have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Ingber, D. E. and Huh, D. "Organ Mimic Device with Microchannels and Methods of Use and Manufacturing Thereof," U.S. Pat. No. 8,647,861, application Ser. No. 13/054,095, filed Jun. 30, 2011, (issued Feb. 11, 2014).
2. Hinojosa, C. D, et al. "Systems and Methods for Improved Performance of Fluidic and Microfluidic Systems," WIPO PCT Patent Publication Number WO/2016/010861, Application PCT/US2015/040026, filed Jul. 10, 2015. (published Jan. 21, 2016).

We claim:

1. A method of functionalizing the surface of a microfluidic channel comprising the steps of:
    a) providing;
        i) an enclosed microfluidic channel comprising an unmodified surface;
        ii) a bifunctional crosslinker selected from the group consisting of ANB-NOS, Sulfo-SAND, SANPAH and Sulfo-SANPAH;
        iii) surface hydrophobicity modifying molecules selected from the group consisting of PEG, TRIS, poly vinyl alcohol, and PLA;
    b) exposing at least a portion of said unmodified surface to said bifunctional crosslinker;
    c) activating said crosslinker under first conditions to create a crosslinked; and
    d) exposing said crosslinked surface to said surface hydrophobicity modifying molecules under second conditions to create a functionalized surface.

2. The method of claim 1, wherein said enclosed microfluidic channel is a portion of a microfluidic device.

3. The method of claim 1, wherein said enclosed microfluidic channel is.

4. The method of claim 1, wherein said enclosed microfluidic channel further comprises a bubble.

5. The method of claim 4, further comprising the step of clearing said bubble from said enclosed microfluidic channel.

6. The method of claim 1, wherein said activating of step c) is done without added heat.

7. The method of claim 1, wherein said PEG is an amine-terminated PEG.

8. The method of claim 1, further comprising step e) seeding said enclosed microfluidic channel with cells.

9. The method of claim 8, wherein said functionalized surface prevents cell attachment.

10. The method of claim 8, wherein said functionalized surface promotes cell attachment.

11. The method of claim 8, wherein said unmodified surface of step a) comprises naturally occurring moieties selected from the group consisting of double bonds, C—H sites, N—H sites, and nucleophiles.

12. The method of claim 11, wherein said nucleophiles are selected from the group consisting of primary amines, alcohols, azide, amines, and amides.

13. The method of claim 1, further comprising the step of masking at least a region of said unmodified surface of said channel so as to create a masked portion and an unmasked portion.

14. The method of claim 1, wherein said unmodified surface comprises PDMS.

15. The method of claim 14, wherein said first conditions comprise exposing said crosslinker to light.

16. The method of claim 15, wherein said exposure to light comprises rastering or pattern projection.

* * * * *